United States Patent [19]

Shturman

[11] Patent Number: 5,554,163
[45] Date of Patent: Sep. 10, 1996

[54] ATHERECTOMY DEVICE

[75] Inventor: Leonid Shturman, Minnetonka, Minn.

[73] Assignee: Shturman Cardiology Systems, Inc., Minneapolis, Minn.

[21] Appl. No.: 429,626

[22] Filed: Apr. 27, 1995

[51] Int. Cl.$^6$ ..................................................... A61B 17/32
[52] U.S. Cl. ........................... 606/159; 606/170; 604/22
[58] Field of Search ................................. 606/159, 170, 606/171, 180; 604/22; 128/772

[56]  References Cited

U.S. PATENT DOCUMENTS

| Re. 33,569 | 4/1991 | Gifford, III et al. . | |
|---|---|---|---|
| 4,627,436 | 12/1986 | Leckrone . | |
| 4,669,469 | 6/1987 | Gifford, III et al. . | |
| 4,781,186 | 11/1988 | Simpson et al. . | |
| 4,979,951 | 12/1990 | Simpson . | |
| 4,990,134 | 2/1991 | Auth . | |
| 5,047,040 | 9/1991 | Simpson et al. | 606/159 |
| 5,053,044 | 10/1991 | Mueller et al. . | |
| 5,092,873 | 3/1992 | Simpson et al. . | |
| 5,100,424 | 3/1992 | Jang et al. . | |
| 5,190,046 | 3/1993 | Shturman . | |
| 5,312,427 | 5/1994 | Shturman . | |
| 5,314,438 | 5/1994 | Shturman | 606/159 |
| 5,331,947 | 7/1994 | Shturman . | |
| 5,356,418 | 10/1994 | Shturman . | |
| 5,360,432 | 11/1994 | Shturman | 606/159 |
| 5,366,464 | 11/1994 | Belknap | 606/159 |

OTHER PUBLICATIONS

Fishman, Robert F. and Baim, Donald S., "Coronary Atherectomy," *Practical Angioplasty*, David P. Faxon, M.D., Editor, Section of Cardiology, The University Hospital, Boston University Medical Center, Boston, MA 02118, pp. 179–195.

*Primary Examiner*—Michael Powell Buiz
*Assistant Examiner*—William Lewis
*Attorney, Agent, or Firm*—Gregory P. Kaihoi

[57] ABSTRACT

A rotational atherectomy device having directional control for selectively removing tissue from an artery (or other bodily passageway or cavity). The atherectomy device includes a rotational atherectomy apparatus having a flexible, elongated drive shaft disposed in the lumen of a catheter. A central portion of an intermediate segment of the drive shaft is coated with an abrasive material to define an abrasive segment of the drive shaft. The drive shaft has a central lumen for receipt of a guide wire therein, and around which the drive shaft may be rotated. The guide wire has an intermediate portion with a predetermined curved positioning portion such that when the abrasive segment of the drive shaft is located along the curved positioning portion of the guide wire, such curved positioning portion of the guide wire urges the abrasive segment of the drive shaft laterally. The catheter has an elongated aperture in its side wall, the aperture having a width permitting the abrasive segment of the drive shaft to extend through it so that when the abrasive segment of the drive shaft and the curved positioning portion of the guide wire are both aligned with the aperture, then the curved positioning portion of the guide wire urges the abrasive segment of the drive shaft laterally out through the catheter aperture to engage tissue to be removed from the bodily passageway or cavity. In a preferred embodiment, the catheter includes two lumens, one for a conventional guide wire and the other for a separate positioning wire having the predetermined curved positioning portion for laterally positioning the abrasive segment of the drive shaft.

77 Claims, 26 Drawing Sheets

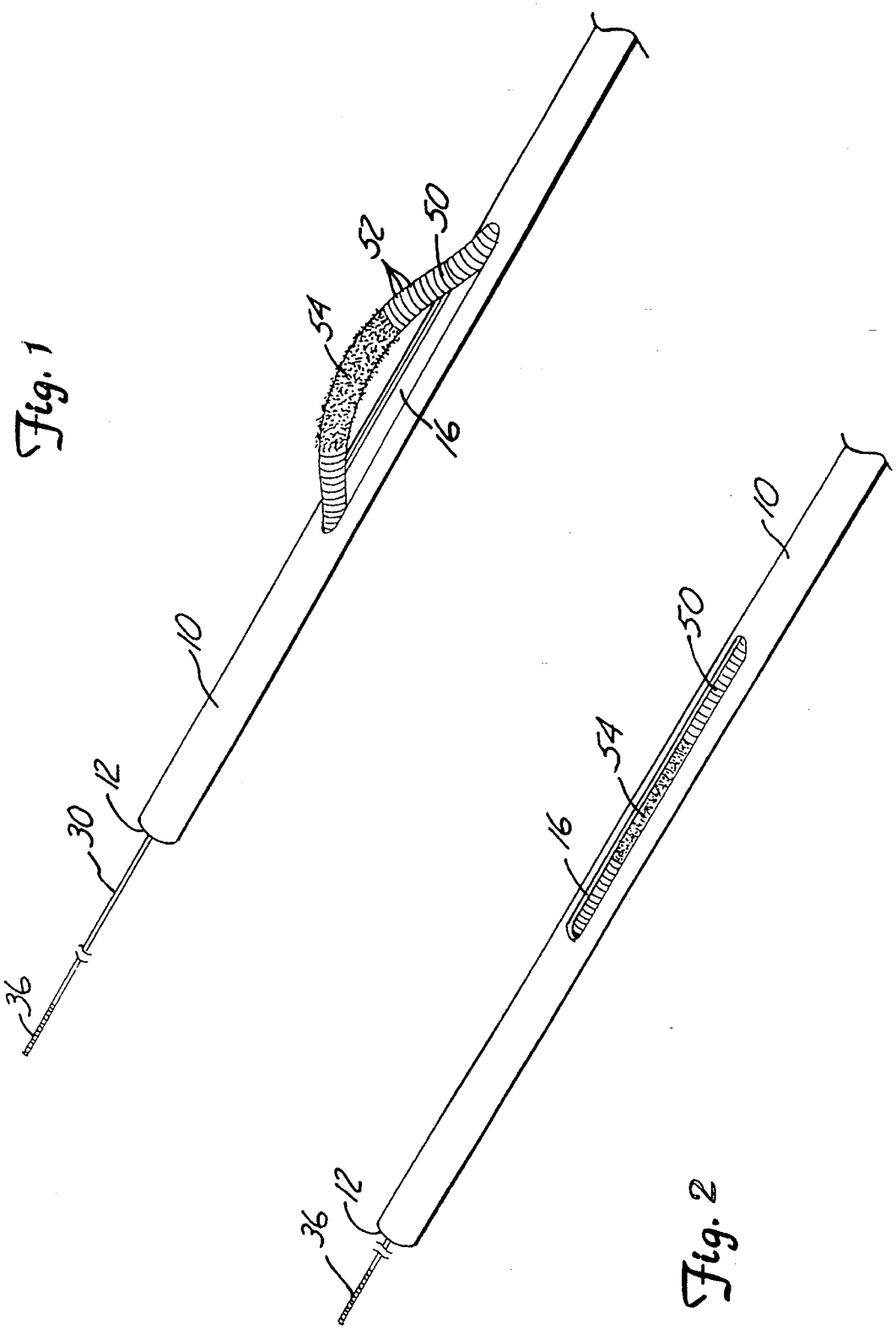

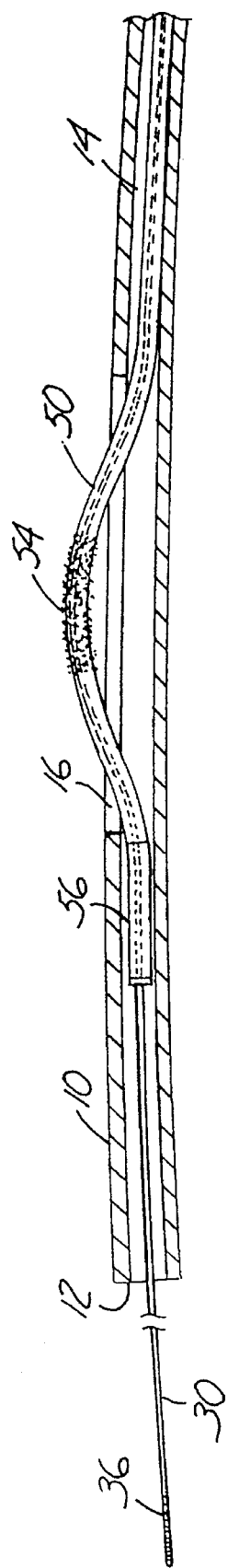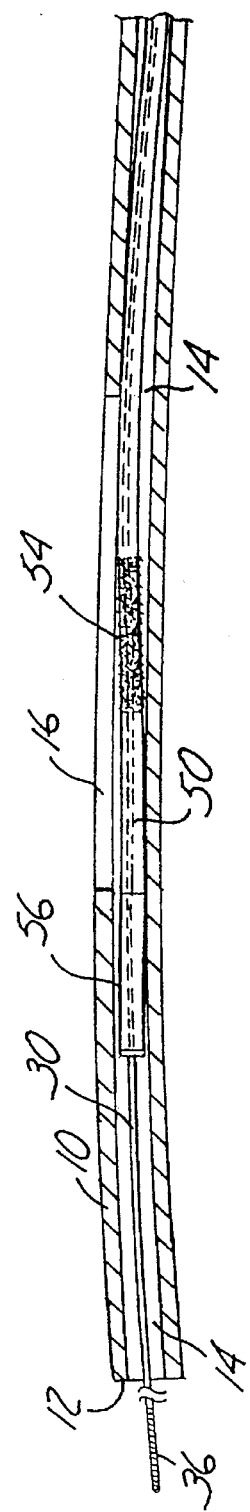

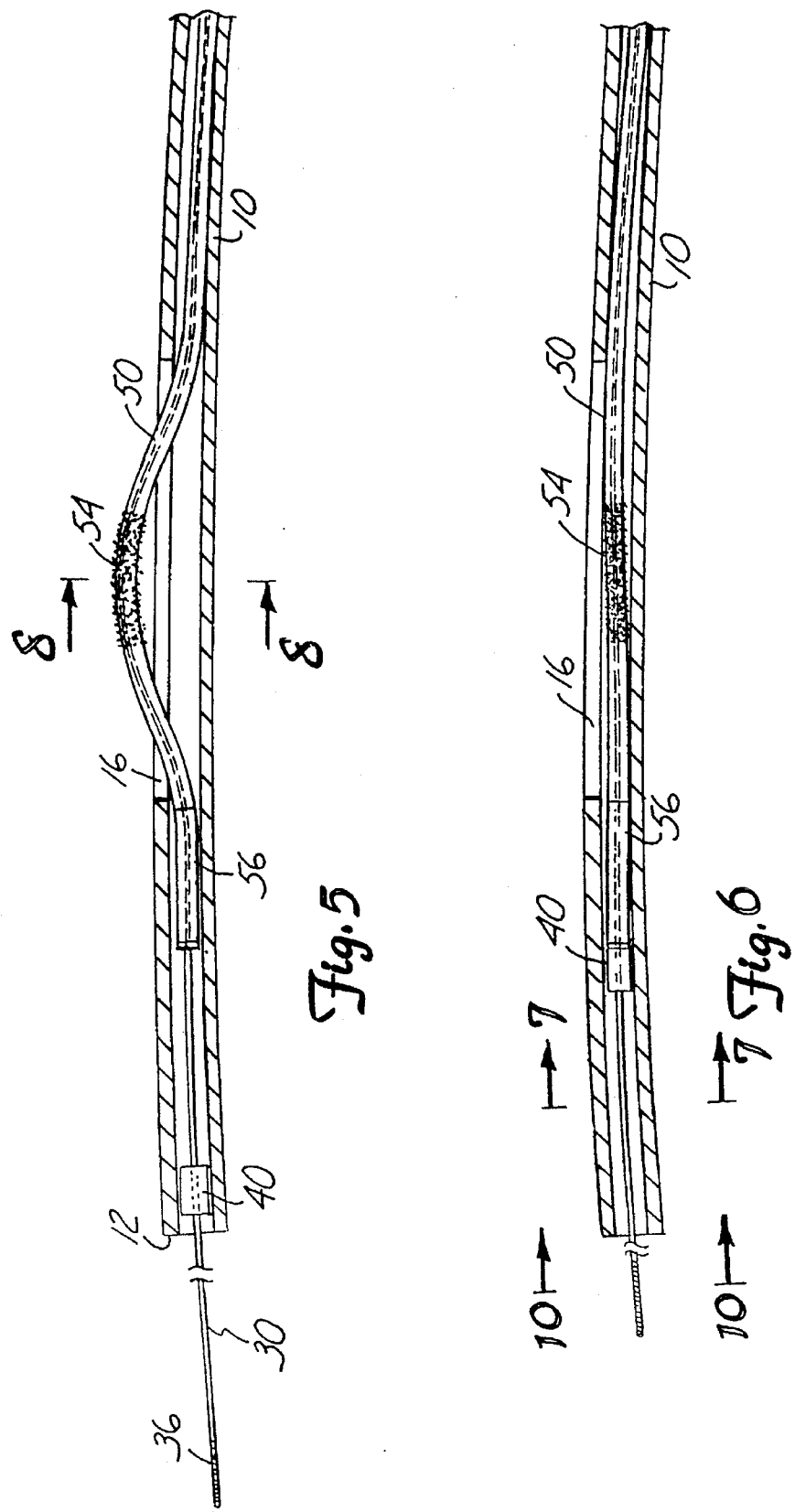

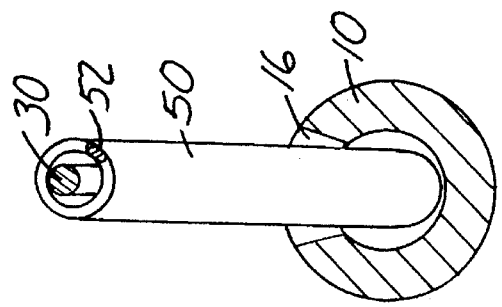
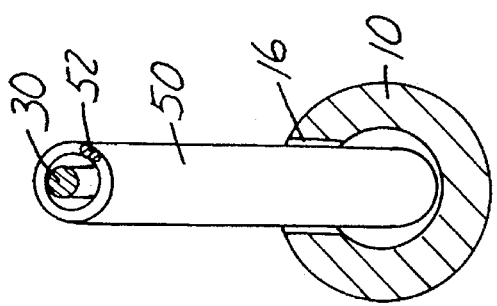
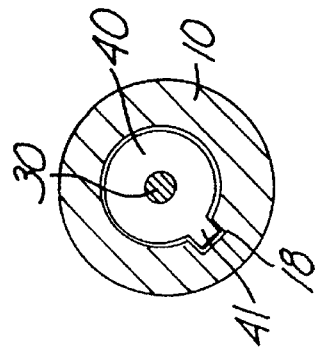
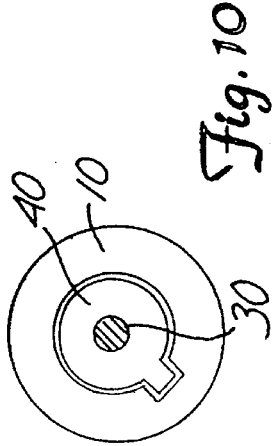

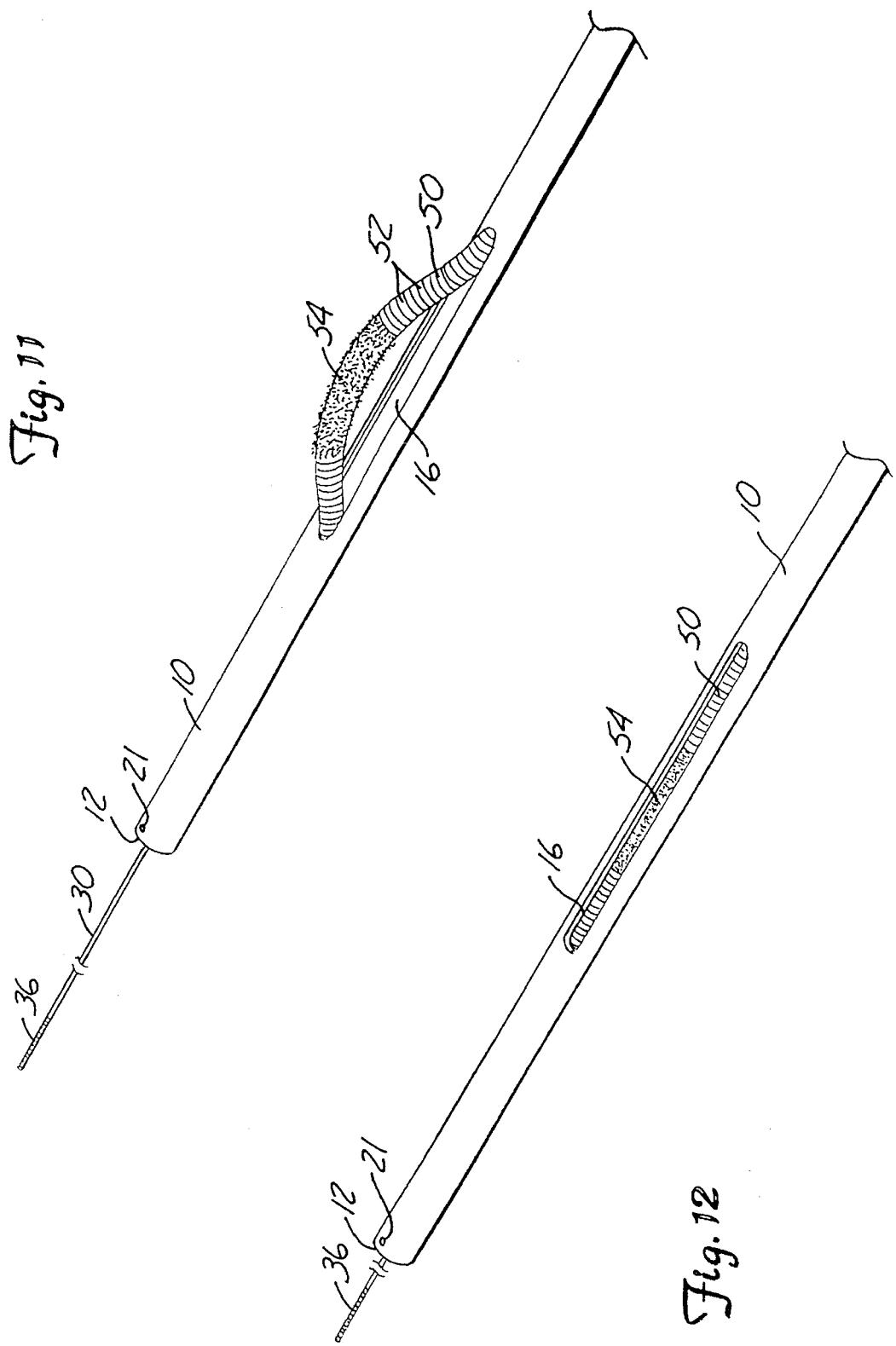

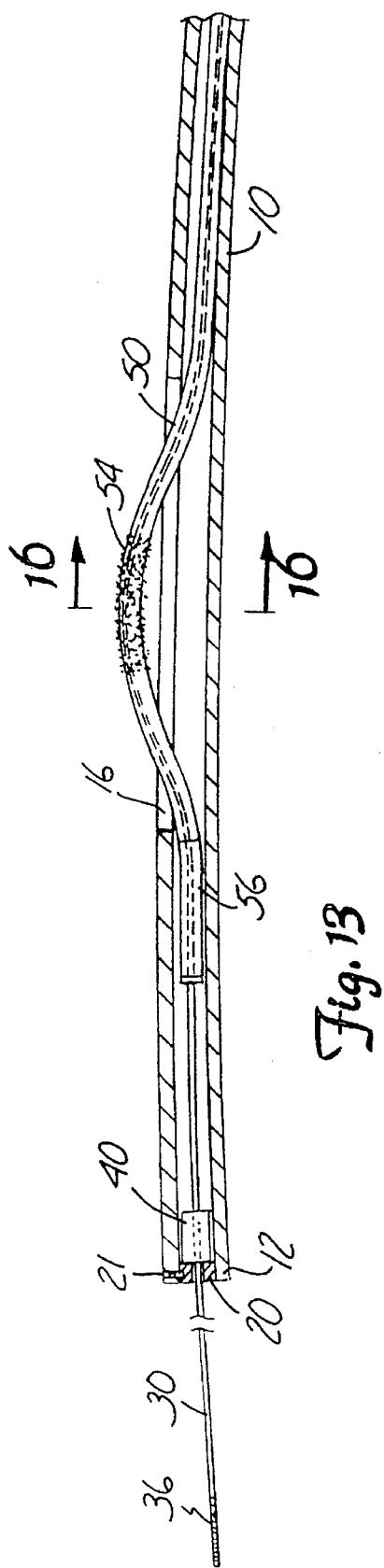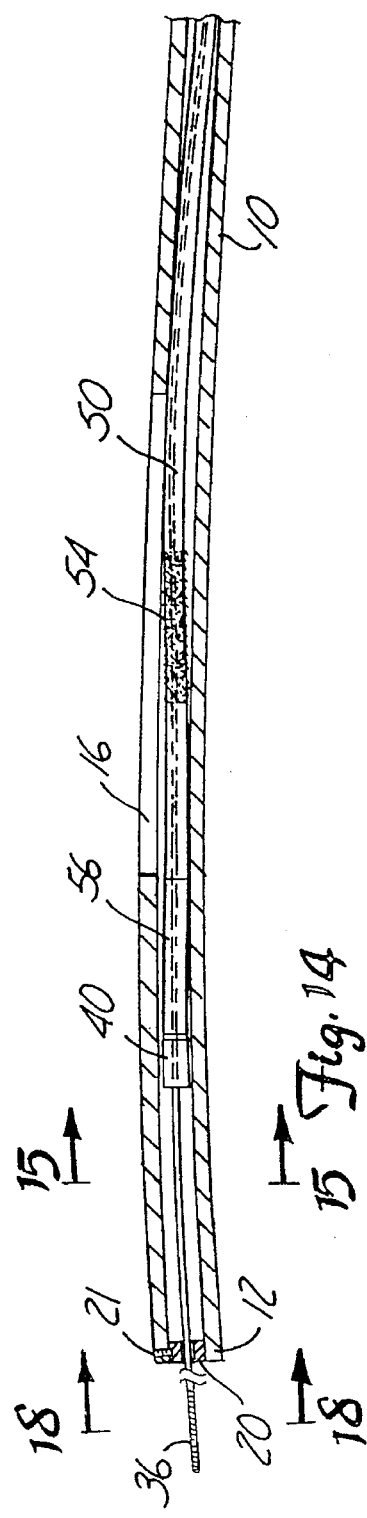

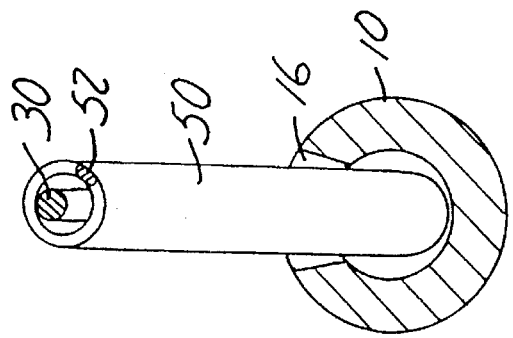
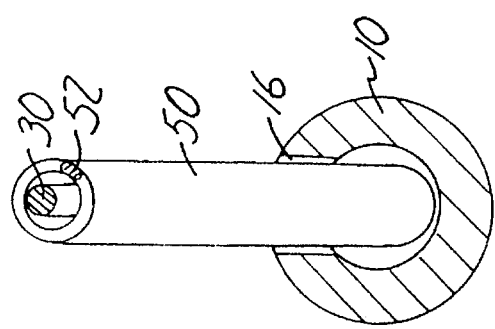
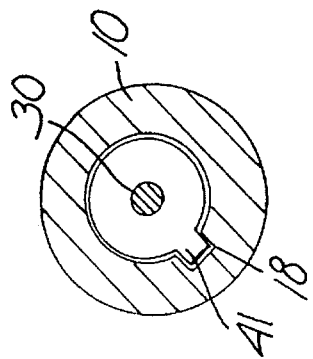
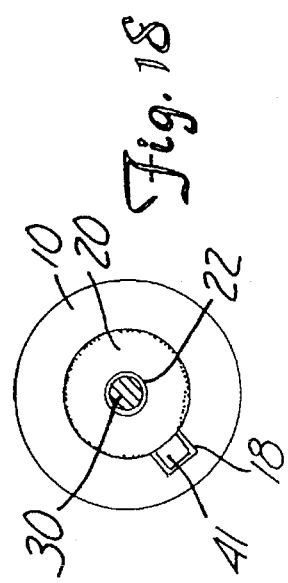

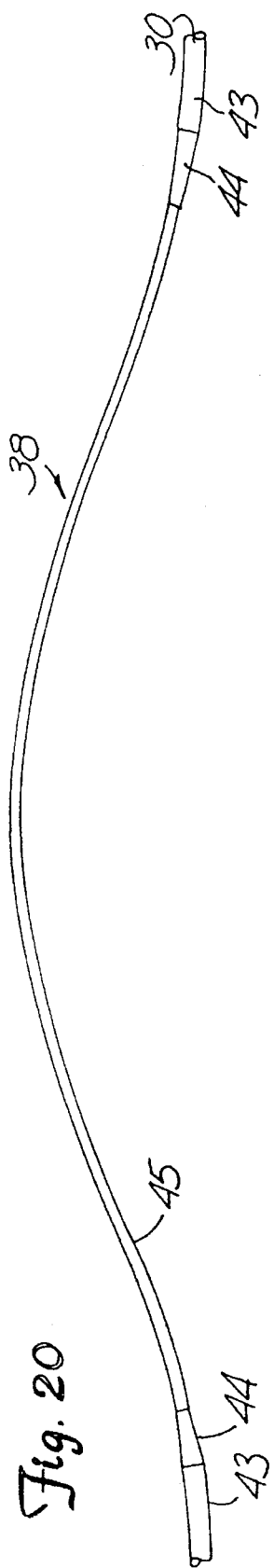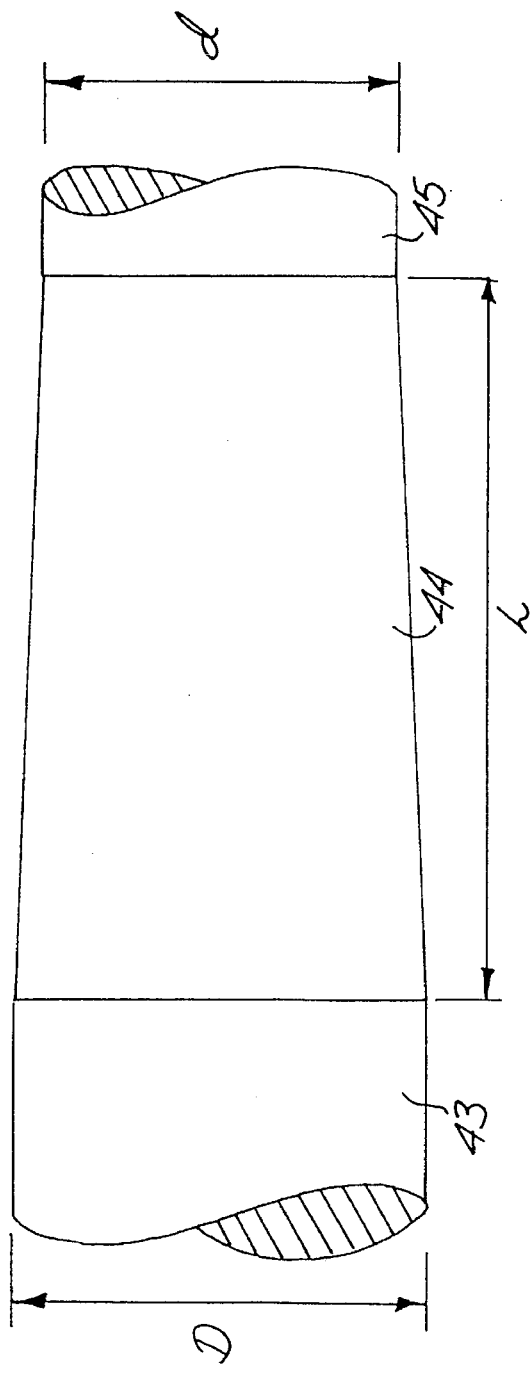

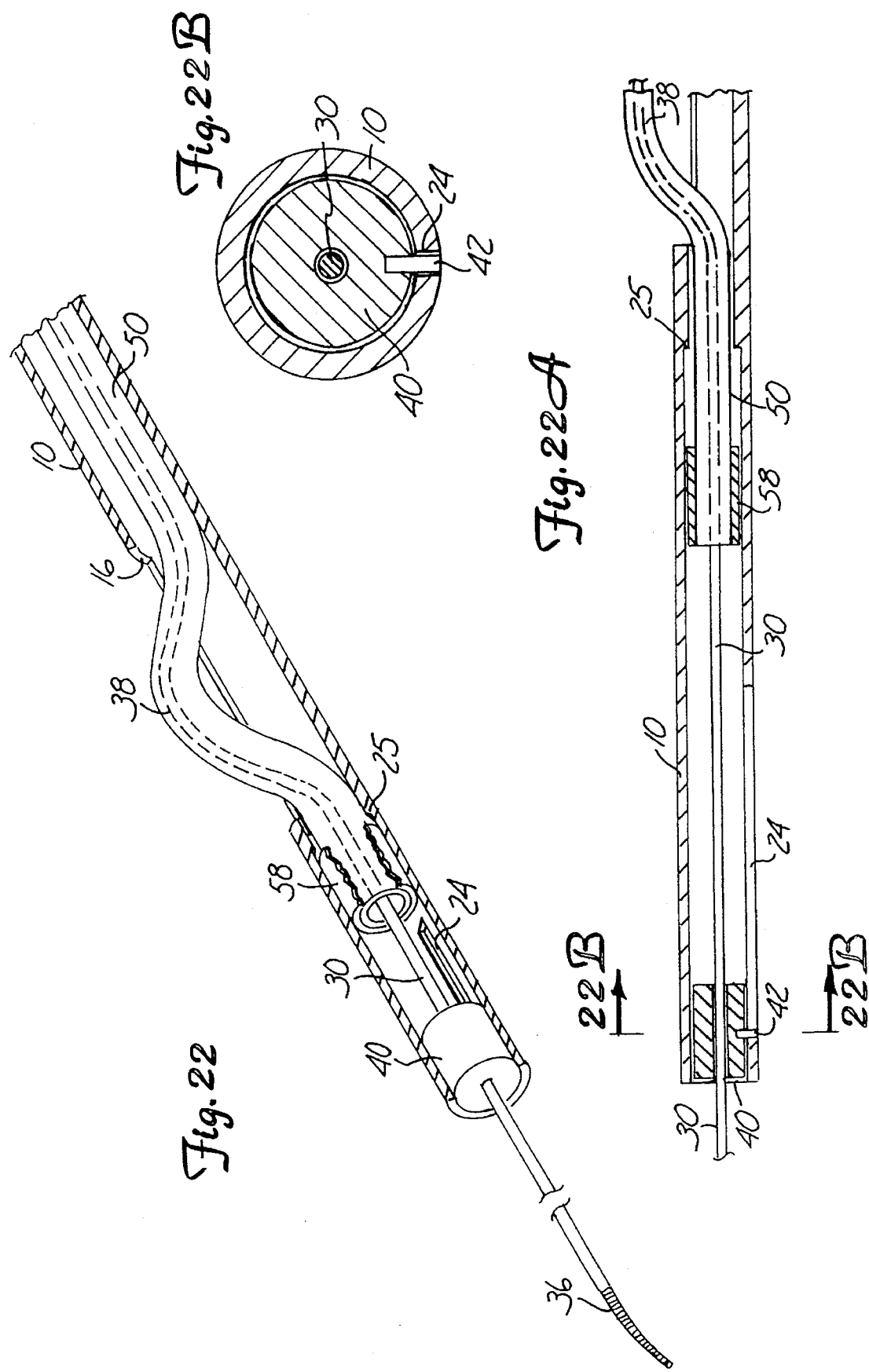

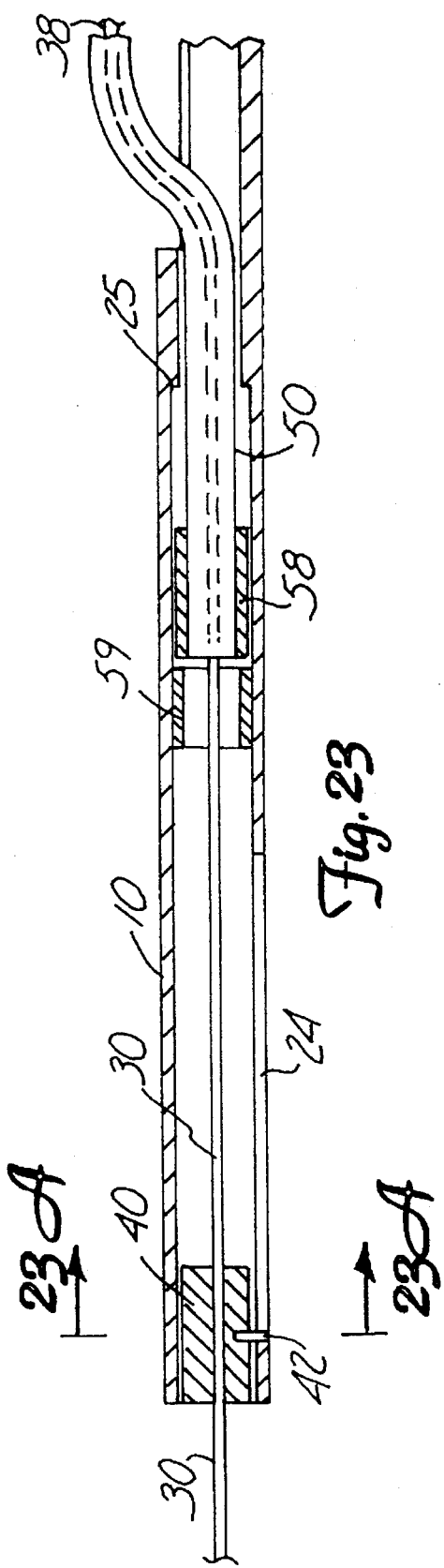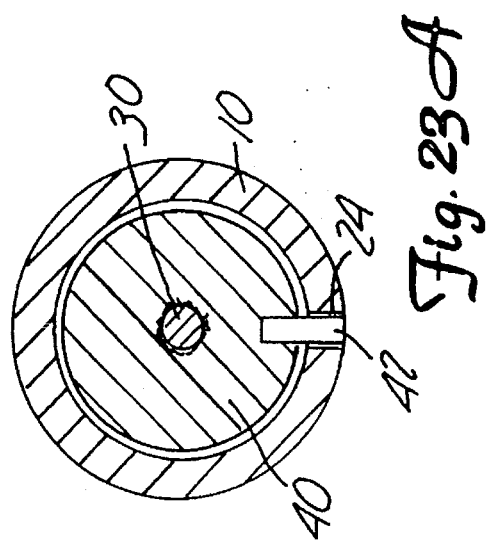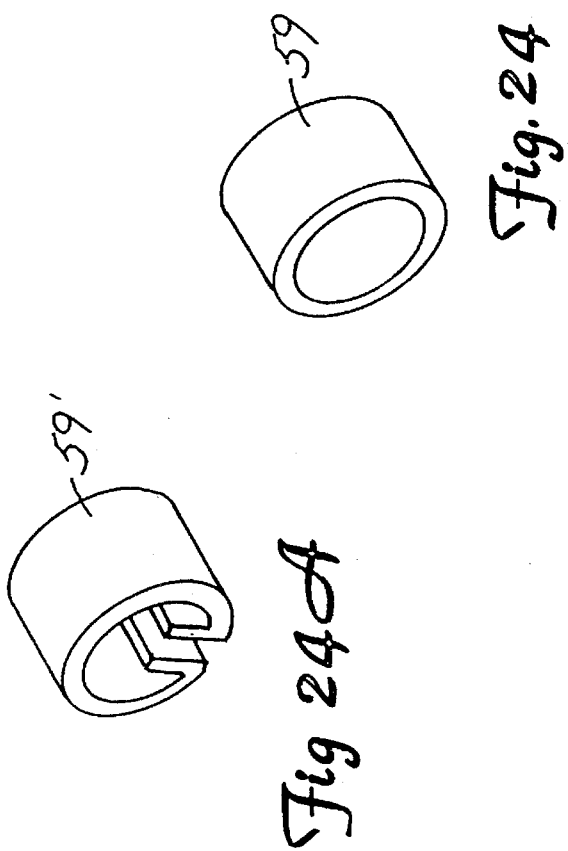

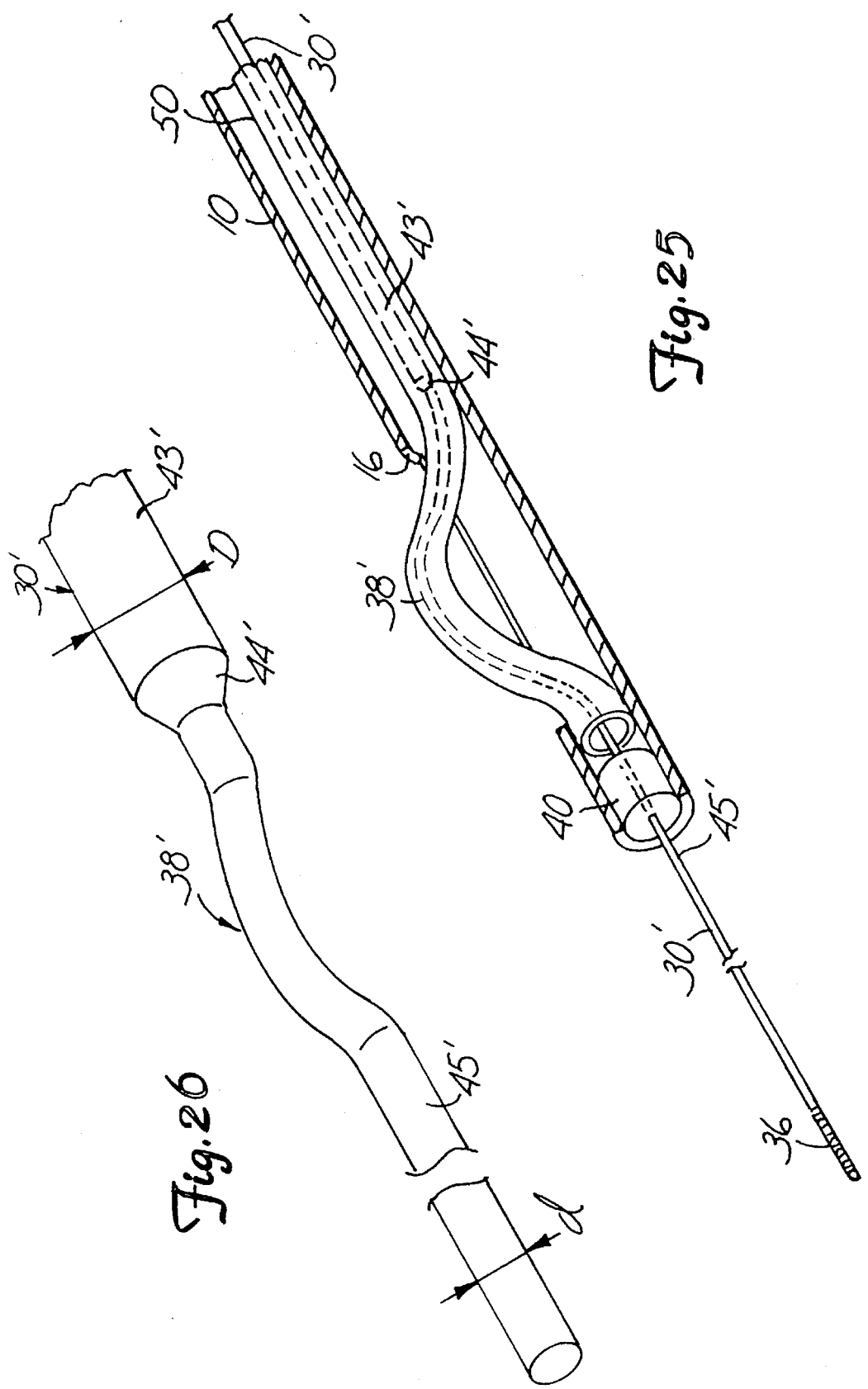

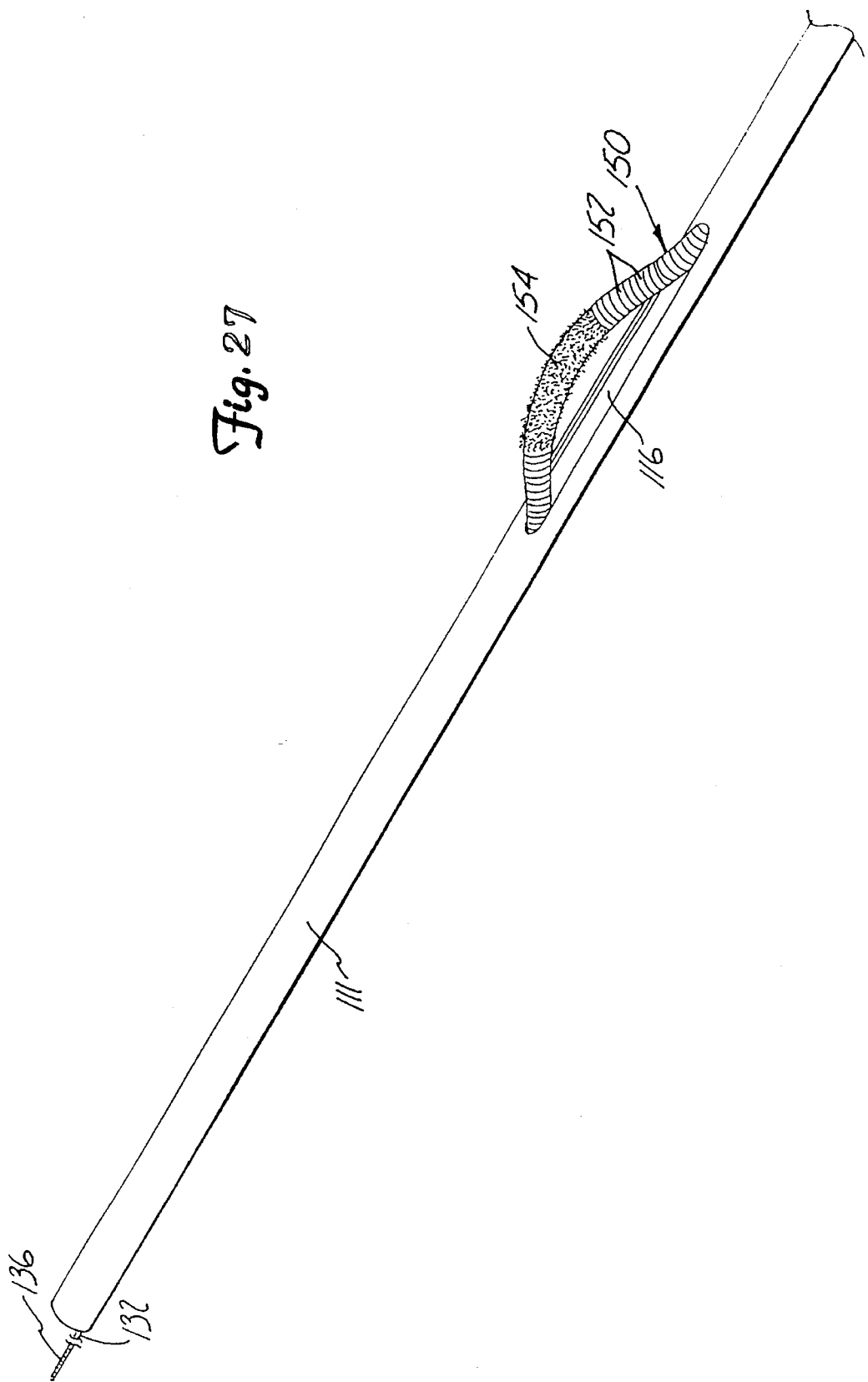

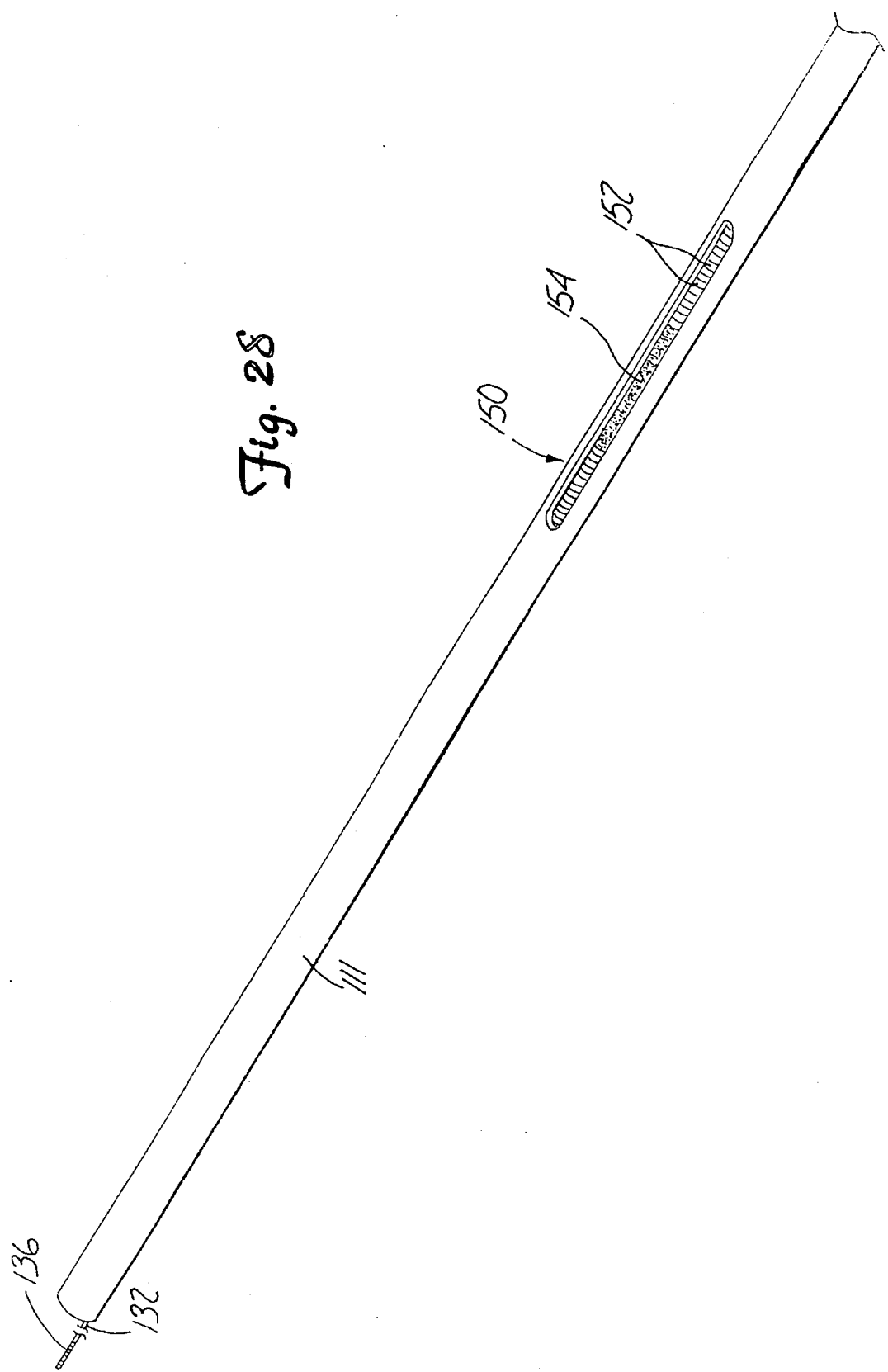

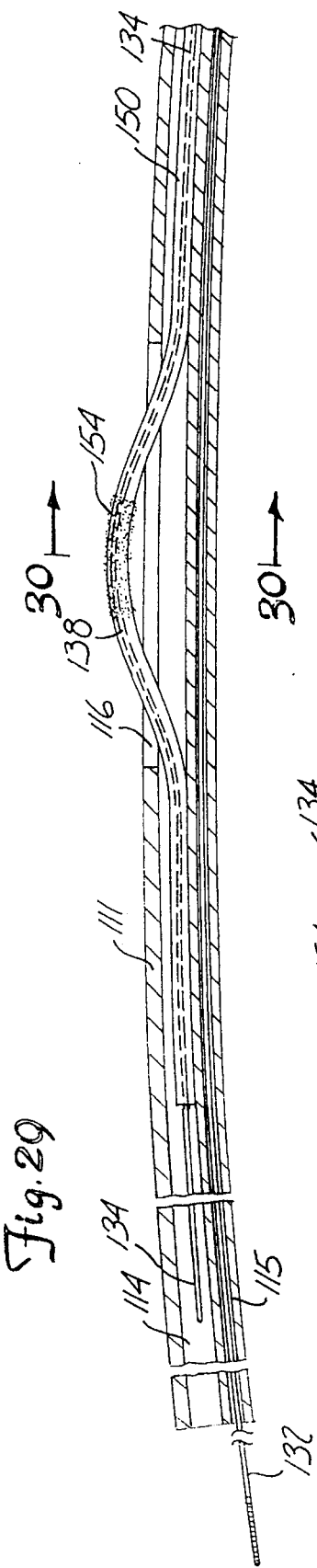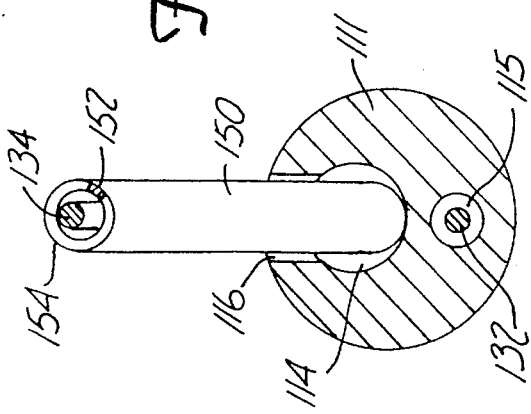

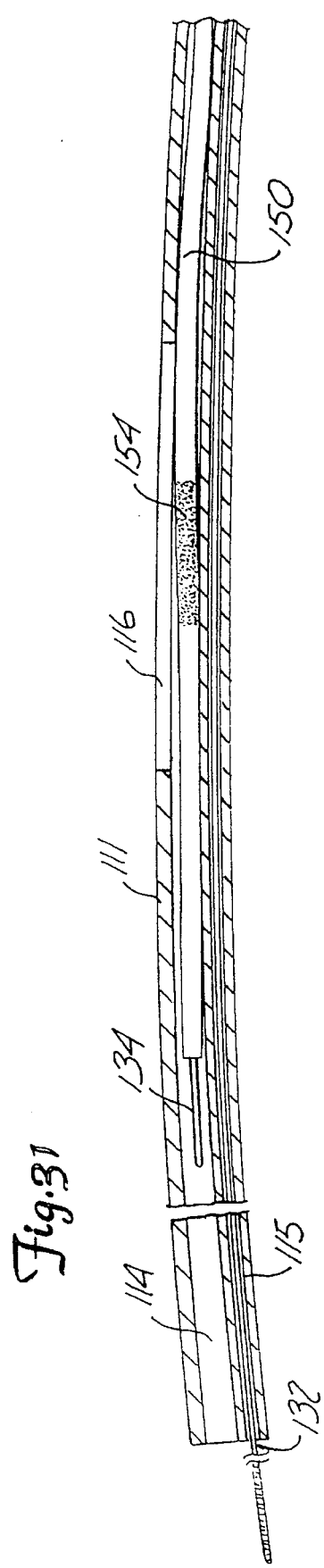

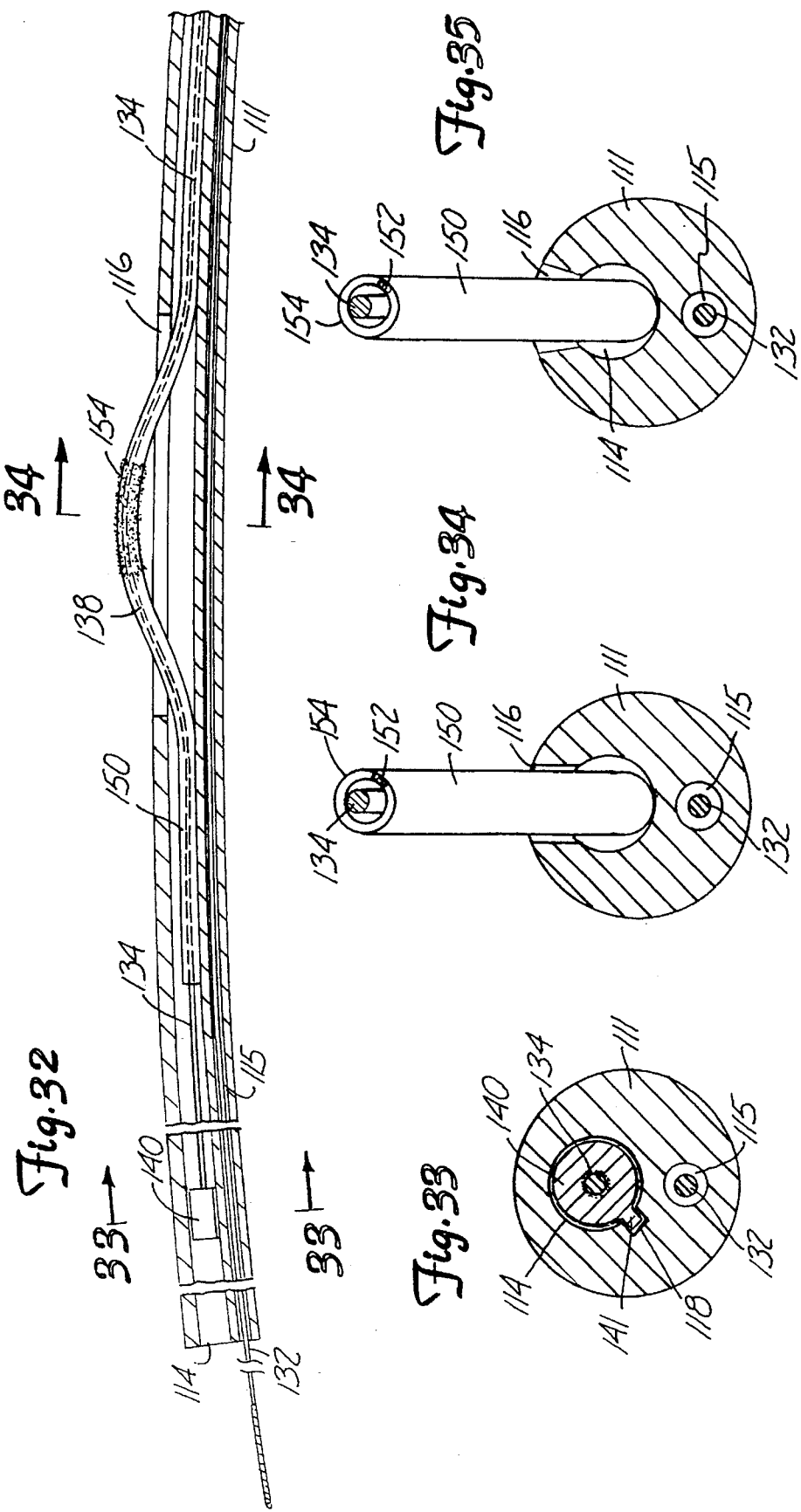

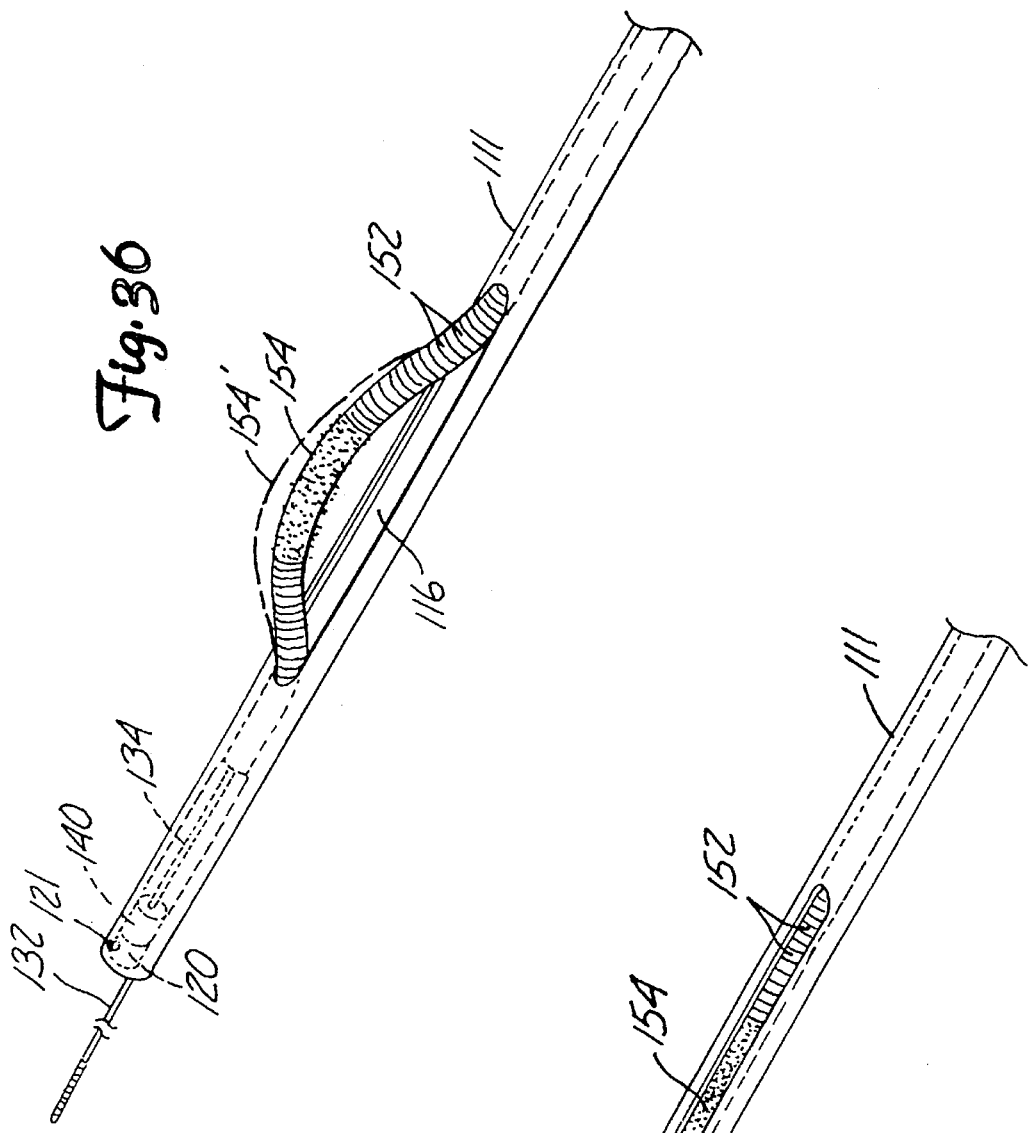

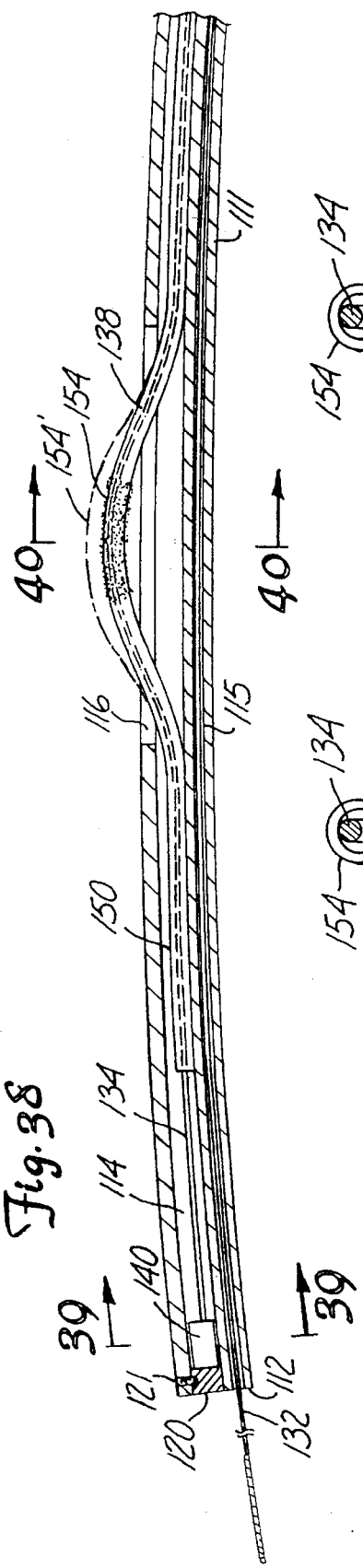
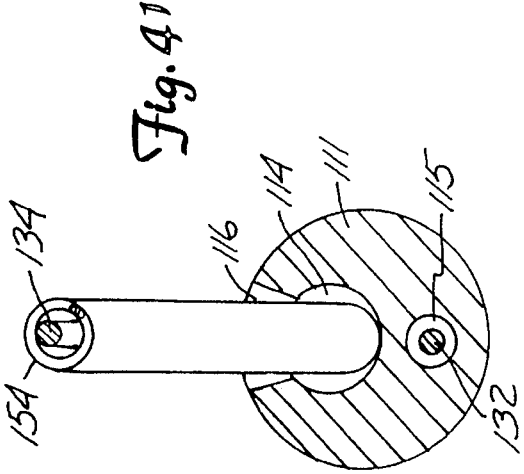
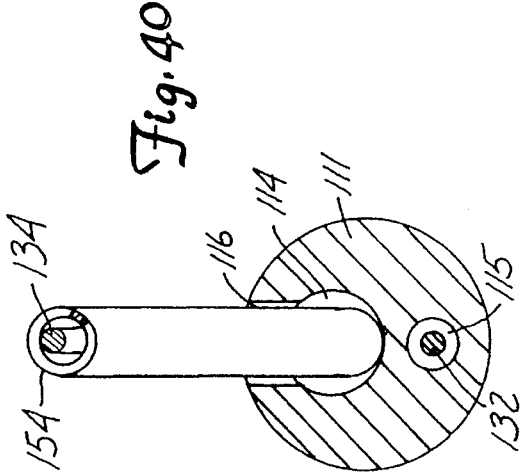
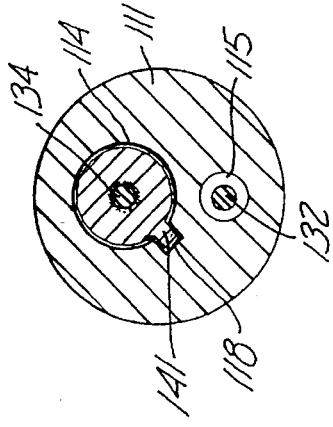

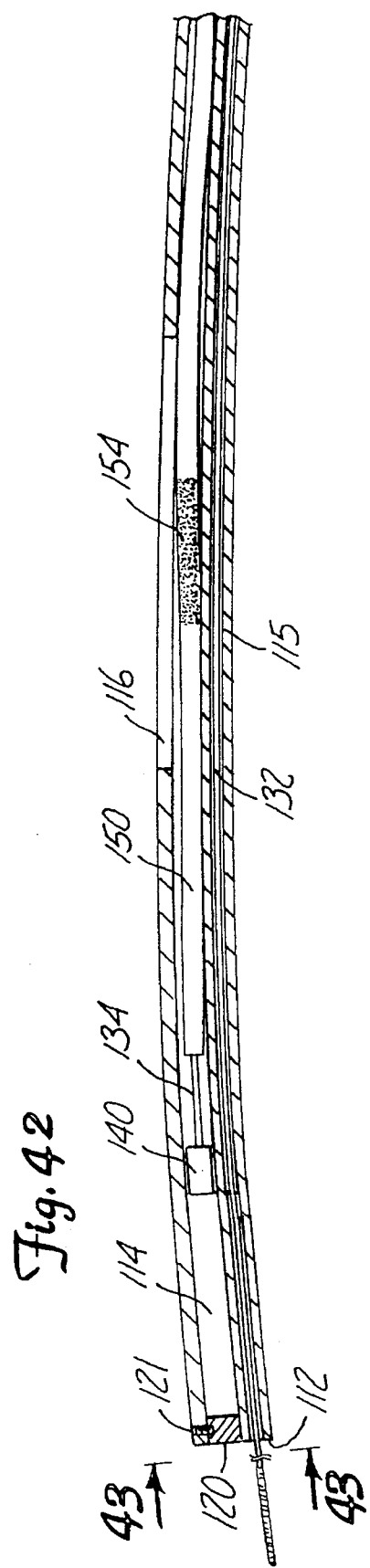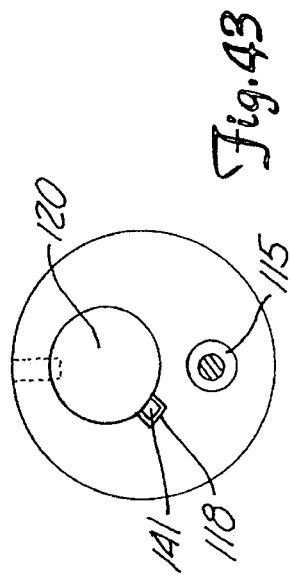

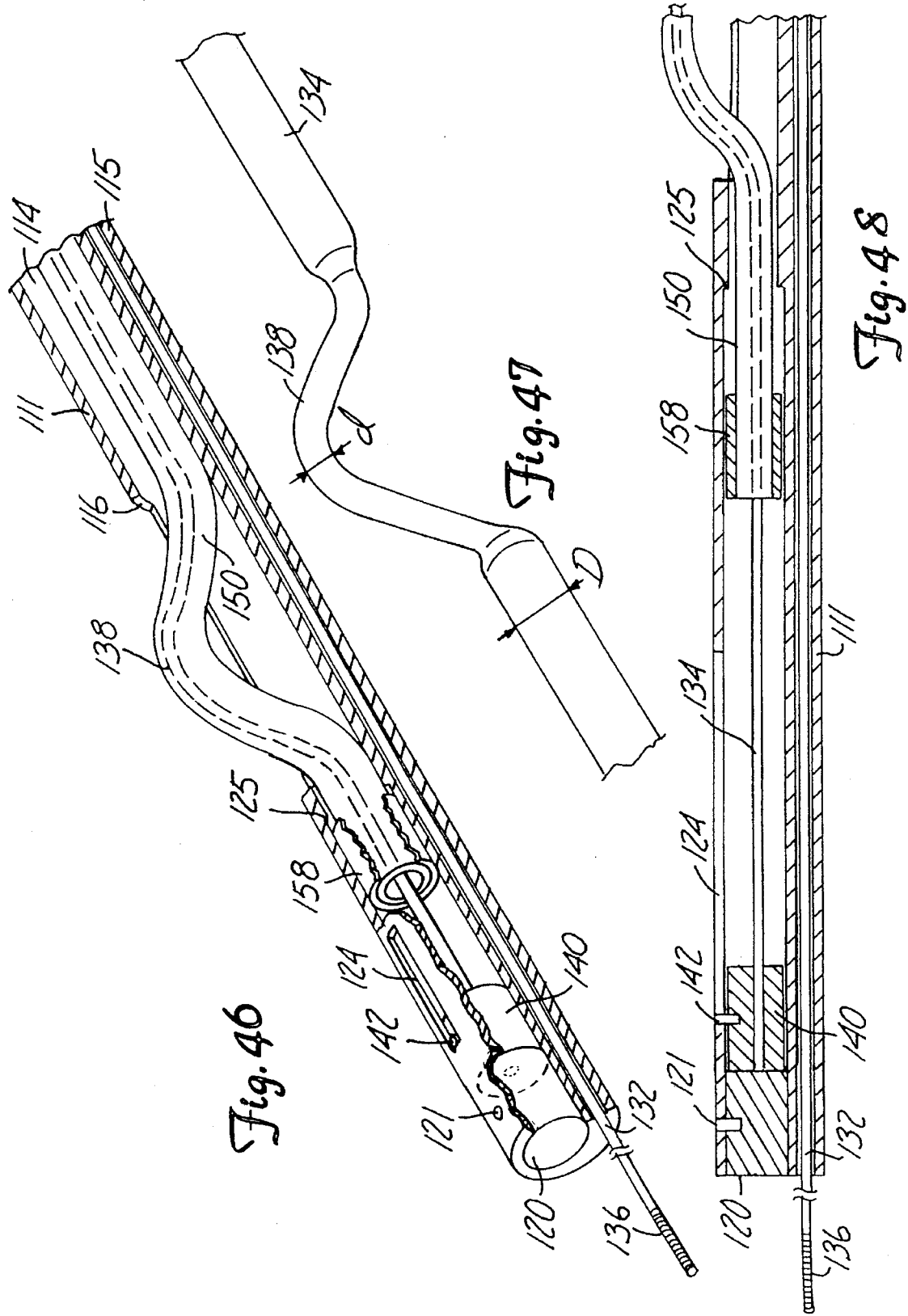

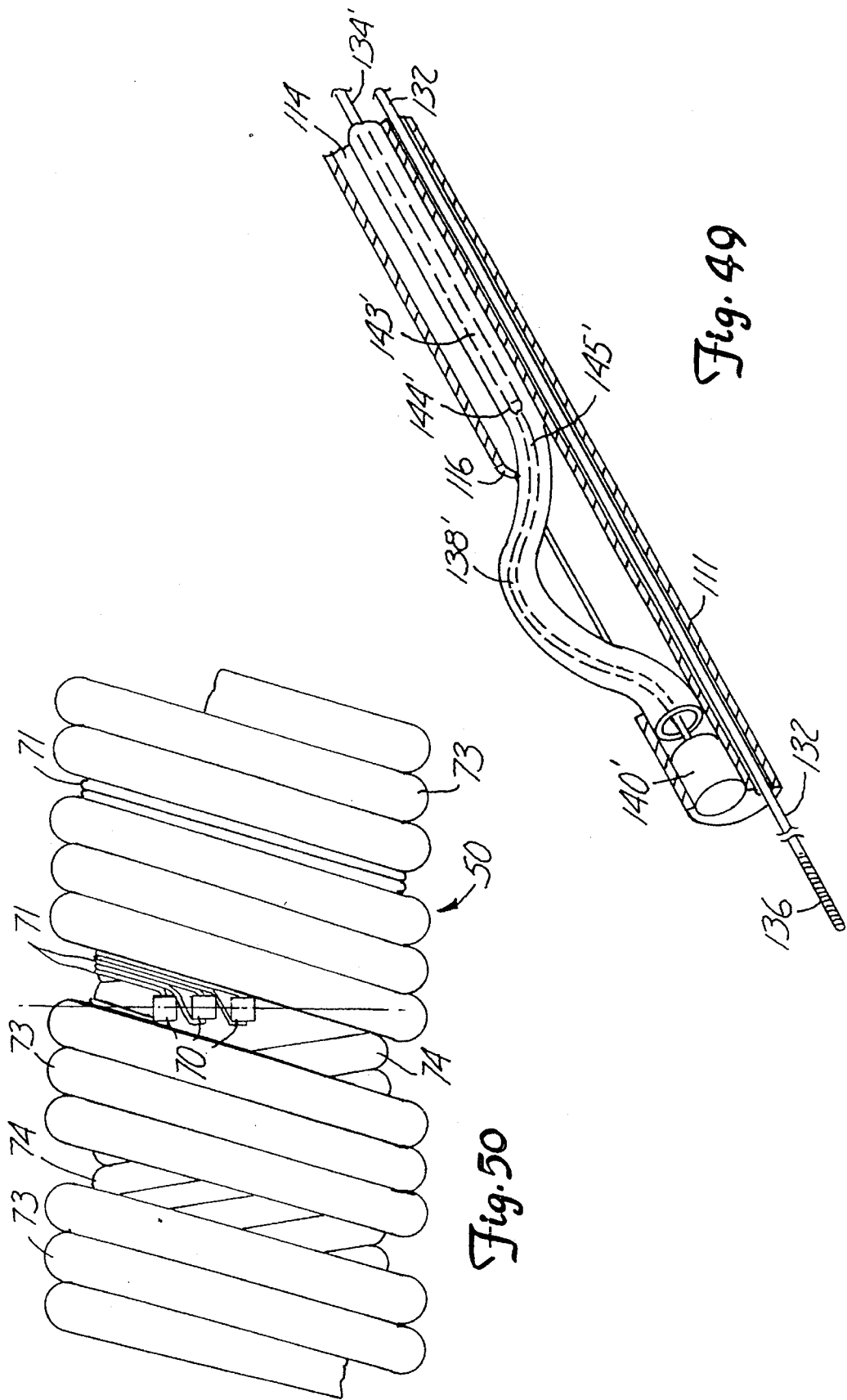

ATHERECTOMY DEVICE

FIELD OF THE INVENTION

The invention relates to devices and methods for removing tissue from body passageways, such as removal of atherosclerotic plaque from arteries, utilizing a rotary atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft cholesterol-rich atheromatous material hardens into a calcified atherosclerotic plaque. Such atheromas restrict the flow of blood, and therefore are often referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 5,092,873 (Simpson), a cylindrical housing, carried at the distal end of a catheter, has a portion of its side-wall cutout to form a hollow housing into which the atherosclerotic plaque can protrude when the device is positioned next to the plaque. An atherectomy blade, disposed within the housing, is then advanced the length of the housing to lance the portion of the atherosclerotic plaque that extends into the housing cavity. While such devices provide for directional control in selection of tissue to be excised, the length of the portion excised at each pass of the atherectomy blade is necessarily limited to the length of the cavity in the device-in turn, the length and relative rigidity of the housing limits the maneuverability and therefore the utility of the device in narrow and tortuous arteries such as coronary arteries.

Another approach which solves some of the problems relating to removal of atherosclerotic plaque in narrow and tortuous passageways involves the use of an abrading device carried at the distal end of a flexible drive shaft. Examples of such devices are illustrated in U.S. Pat. No. 4,990,134 (issued to Auth), and 5,314,438 (issued to Shturman). In the Auth device, abrasive material such as diamond grit (diamond particles or dust) is deposited on a rotating burr carried at the distal end of a flexible drive shaft. In the Shturman device, a thin layer of abrasive particles is bonded directly to the wire turns of an enlarged diameter segment of the drive shaft. The abrading device in such systems is rotated at speeds up to 200,000 rpm or more, which, depending on the diameter of the abrading device utilized, can provide surface speeds of the abrasive particles in the range of 40 ft/sec. Auth claims that at surface speeds below 40 ft/sec his abrasive burr will remove hardened atherosclerotic material but will not damage normal elastic soft tissue of the vessel wall. Auth also admits that at surface speeds above 40 ft/sec the abrasive burr will remove both hardened and soft tissue. See, e.g., Pat. No. 4,990,134 at col. 3, lines 20–23.

Not all atherosclerotic plaques are hardened, calcified atherosclerotic plaques, however. Moreover, the mechanical properties of soft plaques are very often quite close to the mechanical properties of the soft wall of the vessel. Thus, one cannot always rely entirely on the differential cutting properties of such abrasives to remove atherosclerotic material from an arterial wall, particularly where one is attempting to entirely remove all or almost all of the atherosclerotic material.

Moreover, a majority of atherosclerotic lesions are asymmetrical (i.e., the atherosclerotic plaque is thicker on one side of the artery than on the other). Since the stenotic material will be entirely removed on the thinner side of an eccentric lesion before it will be removed on the other, thicker side of the lesion, during removal of the remaining thicker portion of the atherosclerotic plaque the abrasive burr of the Auth device or the abrasive-coated enlarged diameter segment of the drive shaft of the Shturman device necessarily will be engaging healthy tissue on the side which has been cleared. Indeed, lateral pressure by such healthy tissue against the abrading device is required to keep the abrading device in contact with the remaining stenotic tissue on the opposite wall of the passageway. For stenotic lesions that are entirely on one side of an artery (a relatively frequent condition), this means that the healthy tissue across from the stenotic lesion will be exposed to and in contact with the abrading device for substantially the entire procedure. Moreover, pressure from that healthy tissue against the abrading device will be, in fact, the only pressure urging the abrading device against the atherosclerotic plaque. Under these conditions, a certain amount of damage to the healthy tissue is almost unavoidable, even though undesirable, and there is a clear risk of perforation. In some cases, this "healthy tissue" across from a stenotic lesion may itself be somewhat hardened (i.e., it has diminished elasticity); under such circumstances, the differential cutting phenomenon described by Auth will also be diminished, resulting in a risk that this "healthy" tissue may also be removed, potentially causing perforation. Thus, in today's clinical practice (balancing safety and residual stenosis), physicians rarely use Auth-type burr diameters as large as they would otherwise may prefer to utilize.

The Shturman device described in U.S. Pat. No. 5,314,438, provides a more flexible abrading device and the possibility of ultrasonic imaging of the atherosclerotic plaque and the vascular wall at the time of plaque removal, but still does not provide for the positioning of the abrading device against one side of the arterial wall (i.e., against the atherosclerotic plaque) without simultaneously contacting the opposite side of the arterial wall.

In a prior patent of Applicant's, U.S. Pat. No. 5,356,418, incorporated herein by reference (the "'418 patent"), Shturman described a rotational atherectomy apparatus with a special guide wire that can position an abrasive burr against eccentric plaque located only on one side of an arterial wall without simultaneously contacting the opposite side of the arterial wall. In Shturman's U.S. Pat. No. 5,312,427 (the "'427 Patent"), he describes the use of a two wire system utilizing a conventional guide wire and a positioning wire for laterally positioning an abrasive burr against eccentric plaque so that the abrasive burr contacts only the eccentric plaque and does not contact the opposing wall of the artery. This two-wire system utilizes a dual lumen catheter, a conventional guide wire disposed in one of the lumens, and a flexible drive shaft disposed over a special positioning wire in the other lumen. The positioning wire includes a pre-shaped positioning segment for laterally positioning the abrasive burr. When the flexible drive shaft with its abrasive burr is extended distally of the catheter and the special pre-shaped, curved section of the positioning wire is aligned with the abrasive burr the positioning segment of the positioning wire laterally deflects the abrasive device to provide selective control over the lateral position of the abrasive burr within the artery.

In another of Applicant's patents, U.S. Pat. No. 5,360,432 (the "'432 Patent"), incorporated herein by reference, Shturman describes a directional rotational atherectomy device having an abrading device formed by a thin layer of abrasive particles bonded directly to wire turns of a distal segment of a flexible drive shaft. Positioning and manipulation of the flexible abrasive segment of the drive shaft can be accomplished either by utilizing a special guide wire similar to the one described in the '418 Patent, or by utilizing a dual wire system similar to the one described in the '427 Patent.

When the abrasive device of the '427 Patent is rotated against a side of an atherosclerotic artery, torque develops which tends to twist the drive shaft and the positioning wire helically about the guide wire (i.e., the portion of the drive shaft extending distally of the catheter ordinarily is co-planar, but the torque created when the device engages stenotic tissue twists this portion of the drive shaft into a configuration that, rather than co-planar, is roughly helical). This effect becomes more noticeable when the drive shaft and the abrading device are extended further from the distal end of the catheter. This condition also occurs with the two-wire system of the '432 Patent. Similar forces attempt to twist the drive shaft and guide wire of the one-wire system of the '432 Patent and the device described in the '418 Patent.

SUMMARY OF THE INVENTION

The invention provides a rotational atherectomy device having directional control for selectively removing tissue from an artery (or other bodily passageway or cavity). The atherectomy device includes a rotational atherectomy apparatus having a flexible, elongated drive shaft with a proximal segment, an intermediate segment, and a distal segment, a portion of the intermediate segment being coated with an abrasive material to define an abrasive segment of the drive shaft.

In one embodiment, the drive shaft has a central lumen for receipt of a guide wire therein, and around which the drive shaft may be rotated. The guide wire has proximal, intermediate and distal portions, the proximal portion being generally straight, and the intermediate portion having a predetermined curved positioning segment such that when the abrasive segment of the drive shaft is located along the curved positioning segment of the guide wire, such curved segment of the guide wire urges the abrasive segment of the drive shaft laterally.

The device also includes a catheter having walls defining a lumen sized to receive the drive shaft in it. The catheter has proximal, intermediate and distal sections, and the wall of the intermediate section includes an elongated aperture, the aperture having a width and length permitting the abrasive segment of the drive shaft to extend through it so that when the abrasive segment of the drive shaft and the curved positioning segment of the guide wire are both aligned with the aperture, the curved positioning segment of the guide wire urges the abrasive segment of the drive shaft laterally out through the catheter aperture to engage tissue to be removed from the bodily passageway or cavity.

In a preferred embodiment, the catheter includes two lumens, one for a conventional guide wire and the other for the drive shaft which is rotatable around a separate positioning wire having a predetermined curved positioning segment for pushing the abrasive segment of the drive shaft laterally through the elongated aperture in the wall of the catheter.

BRIEF DESCRIPTION OF THE DRAWINGS

FIG. 1 is a perspective, broken-away view of an atherectomy device of the invention;

FIG. 2 is a perspective, broken-away view of the atherectomy device of FIG. 1 with the guide wire and drive shaft in a moved position;

FIG. 3 is a longitudinal cross-sectional view of the atherectomy device of FIG. 1;

FIG. 4 is a longitudinal cross-sectional view of FIG. 2 with the guide wire and drive shaft of the atherectomy device in the moved position of FIG. 2;

FIG. 5 is a longitudinal cross-sectional view of another embodiment of the atherectomy device of the invention;

FIG. 6 is a longitudinal cross-sectional view of the atherectomy device of FIG. 5 with the guide wire and drive shaft in a moved position;

FIG. 7 is a cross-sectional view of the atherectomy device of FIG. 6, taken along lines 7—7 thereof;

FIG. 8 is a cross-sectional view of the atherectomy device of FIG. 5, taken along lines 8—8 thereof;

FIG. 9 is a cross-sectional view, similar to FIG. 8, of a modified embodiment of the atherectomy device of the invention;

FIG. 10 is a distal end view of the atherectomy device of FIG. 6, in partial cross section taken along lines 10—10;

FIG. 11 is a perspective, broken-away view of another embodiment of the atherectomy device of the invention;

FIG. 12 is a perspective, broken-away view of the atherectomy device of FIG. 11 with the guide wire and drive shaft in a moved position;

FIG. 13 is a longitudinal cross-sectional view of the atherectomy device of FIG. 12;

FIG. 14 is a longitudinal cross-sectional view of FIG. 12 with the guide wire and drive shaft of the atherectomy device in the moved position of FIG. 12;

FIG. 15 is a cross-sectional view of the atherectomy device of FIG. 14, taken along lines 15—15 thereof;

FIG. 16 is a cross-sectional view of the atherectomy device of FIG. 13, taken along lines 16—16 thereof;

FIG. 17 is a cross-sectional view, similar to FIG. 16, of a modified embodiment of the atherectomy device of the invention;

FIG. 18 is a distal end view of the atherectomy device of FIG. 14, in partial cross section taken along lines 18—18;

FIG. 20 shows an intermediate portion of an alternate embodiment of a guide wire which can be used in the atherectomy device of FIGS. 11–19;

FIG. 21 is an enlarged detail drawing of a portion of the guide wire of FIG. 20;

FIG. 22 is a perspective, partially broken-away view of another embodiment of the atherectomy device of the invention;

FIG. 22A is a longitudinal cross-sectional view of the atherectomy device of FIG. 22;

FIG. 22B is a cross-sectional view of the atherectomy device of FIG. 22A, taken along lines 22B—22B thereof;

FIG. 23 is a longitudinal cross-sectional view, similar to FIG. 22A, of a modified embodiment of the atherectomy device of the invention;

FIG. 23A is a cross-sectional view of the atherectomy device of FIG. 23, taken along lines 23A—23A thereof;

FIG. 24 is a perspective view of the distal stop employed in the embodiment of FIG. 23;

FIG. 24A is a perspective view of an alternate configuration for the distal stop employed in the embodiment of FIG. 23;

FIG. 25 is a perspective, partially broken-away view of an alternate embodiment of the atherectomy device of the invention;

FIG. 26 is a perspective view of a portion of an alternate embodiment of a guide wire usable with an atherectomy device of the type shown in FIG. 25;

FIG. 27 is a perspective, broken-away view of another embodiment of the atherectomy device of the invention;

FIG. 28 is a perspective, broken-away view of the atherectomy device of FIG. 27 with the drive shaft in a moved position;

FIG. 29 is a longitudinal cross-sectional view of the atherectomy device of FIG. 27;

FIG. 30 is a cross-sectional view of the atherectomy device of FIG. 29, taken along lines 30—30 thereof;

FIG. 31 is a longitudinal cross-sectional view of FIG. 28 with the positioning wire and drive shaft of the atherectomy device in the moved position of FIG. 28 (moved in comparison to FIGS. 27 and 29);

FIG. 32 is a longitudinal cross-sectional view of another embodiment of the atherectomy device of the invention:

FIG. 33 is a cross-sectional view of the atherectomy device of FIG. 32, taken along lines 33—33 thereof;

FIG. 34 is a cross-sectional view of the atherectomy device of FIG. 32, taken along lines 34—34 thereof;

FIG. 35 is a cross-sectional view, similar to FIG. 34, of a modified embodiment of the atherectomy device of the invention;

FIG. 36 is a perspective, broken-away view of another embodiment of the atherectomy device of the invention;

FIG. 37 is a perspective, broken-away view of the atherectomy device of FIG. 36 with the positioning wire and drive shaft in a moved position;

FIG. 38 is a longitudinal cross-sectional view of the atherectomy device of FIG. 36;

FIG. 39 is a cross-sectional view of the atherectomy device of FIG. 38, taken along lines 39—39 thereof;

FIG. 40 is a cross-sectional view of the atherectomy device of FIG. 38, taken along lines 40—40 thereof;

FIG. 41 is a cross-sectional view, similar to FIG. 40, of a modified embodiment of the atherectomy device of the invention;

FIG. 42 is a longitudinal cross-sectional view of FIG. 37 with the positioning wire and drive shaft of the atherectomy device in the moved position of FIG. 37 (moved in comparison to FIGS. 36 and 38);

FIG. 43 is a distal end view of the atherectomy device of FIG. 42, in partial cross section taken along lines 43—43;

FIG. 46 is a perspective, partially broken-away view of another embodiment of the atherectomy device of the invention;

FIG. 47 is a perspective, partially broken-away view of an alternate embodiment of a positioning wire which is usable with the atherectomy device of FIG. 46;

FIG. 48 is a longitudinal cross-sectional view of the atherectomy device of FIG. 46;

FIG. 49 is a perspective, partially broken-away view of an alternate embodiment of the atherectomy device of the invention;

FIG. 50 is an enlarged, partially broken-away view of a drive shaft of the invention having ultrasound imaging capability;

DETAILED DESCRIPTION OF THE INVENTION

Figure 19:
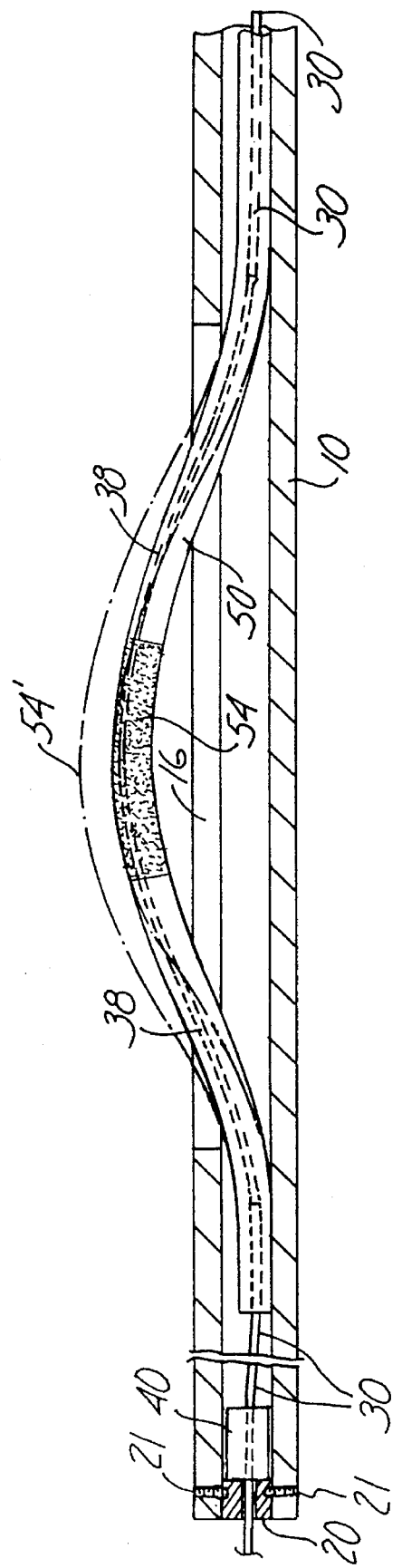
FIG. 19 is a longitudinal cross-sectional view similar to FIG. 13, showing in phantom lines a moved position of the drive shaft.

FIGS. 1–4 illustrate an initial, rudimentary form of the present invention. An elongated catheter 10 has a central lumen 14, in which is disposed a guide wire 30 having a conventional coiled distal tip portion 36. A flexible drive shaft 50 with a central lumen is slidably disposed over the guide wire 30 and within the catheter lumen 14. The drive shaft preferably is of the type made from helically wound wire, the wire turns 52 being depicted in FIGS. 1 and 2, but being omitted from many of the other drawings for the sake of clarity.

The drive shaft 50 is comprised of a proximal segment, an intermediate segment, and a distal segment. As is described in detail in the Shturman U.S. Pat. No. 5,360,432 referred to above, a portion of the intermediate segment of the drive shaft 50 is provided with an abrasive coating 54 to define an abrasive segment of the drive shaft. As is described below, this abrasive segment of the drive shaft abrades tissue to be removed from an artery (such as atherosclerotic plaque) or other bodily passageway or cavity. To reduce friction, portions of the drive shaft contained within the catheter 10 may be provided with low-friction coatings, such as the portion identified by reference number 56 in FIGS. 3–4. The inner surface of the catheter lumen 14 may similarly be coated with low-friction materials; alternately, the catheter itself may be manufactured from materials with a sufficiently low coefficient of friction.

In the embodiment depicted in FIGS. 1–4, the guide wire 30 includes three portions, a generally straight proximal portion, a generally straight distal portion, and an intermediate portion which has a predetermined curved shape defining a positioning portion 38 of the guide wire 30. When the abrasive segment of the drive shaft is located along the curved positioning segment of the guide wire, the curved segment of the guide wire urges the abrasive segment of the drive shaft laterally.

This embodiment of the invention further includes a catheter 10 having a walls defining a lumen 14 sized to receive the drive shaft 50 in it. The catheter has proximal, intermediate and distal sections, and the intermediate section includes an elongated aperture 16 in the wall, the aperture 16 having a width and length permitting the abrasive segment of the drive shaft 50 to extend though it.

As can be seen by comparing FIGS. 1 and 3 with FIGS. 2 and 4, longitudinal movement of the guide wire 30 provides control over the lateral position of the abrasive segment 54 of the drive shaft 50. When the guide wire 30 is retracted with respect to the catheter 10 and drive shaft 50 (see FIGS. 2 and 4), the intermediate curved portion of the guide wire 30 is contained by the lumen 14 of the catheter 10, thus retaining the drive shaft 50 generally within the catheter 10. When the curved intermediate portion of the guide wire 30 is advanced to where it is aligned with the elongated aperture 16 of the catheter 10, however, the curved portion of the guide wire 30 urges the corresponding portion of the flexible drive shaft 50 out through the elongated aperture 16 and into engagement with the tissue desired to be removed. Notice that the movement of the guide wire depicted by comparing FIGS. 3 and 4 is only equal to one-haft about the length of the elongated aperture 16 in the catheter 10—the apex of the curved portion of the guide wire in FIG. 4 is located just slightly proximal to the proximal end of the catheter's elongated aperture, thus giving the drive shaft 50 a slight serpentine configuration in FIG. 4. (Note that outline of the aperture 16 is shown somewhat schematically in FIGS. 3 and 4, as well as in other similar drawings, including FIGS. 5, 6, 13, 14, 19, 29, 31, 32, 38 and 42.)

The guide wire preferably is made of a superelastic shape-memory alloy, such as nitinol. The fabrication of the guide wire from such alloys assures preservation of the predetermined configuration of the curved intermediate portion of the guide wire 30 while permitting it to be advanced around even relatively tortuous curves in a body passageway. The use of such superelastic alloys further makes advancement and retraction of the guide wire 30 easier, and minimizes (or eliminates) any deformation of the catheter (i.e., the catheter can be made relatively flexible while still being stiff enough to not conform to the shape of the guide wire 30).

FIGS. 5–10 depict a slightly different embodiment of the atherectomy device of the invention. In this embodiment, the guide wire includes alignment means for rotationally aligning the curved positioning portion of the guide wire 30 with the catheter's elongated aperture 16. Although means for accomplishing this rotational alignment could be provided in several ways, in a preferred embodiment the alignment means comprises a key and keyway, one of which is associated with the guide wire 30 and the other of which is associated with the catheter 10, thereby rotationally aligning the guide wire with the catheter. FIGS. 5–10 depict a cylindrical slider 40 having an integral key 41 received in a complimentary keyway 18 formed in the wall of the catheter 10. This configuration could be reversed, but the configuration depicted provides for relatively easier manufacturing. For purposes of clarity, the keyway is not shown in FIGS. 5–6 (or in similar drawings of other embodiments), but is shown in transverse cross-section in FIGS. 7 and 10 (and other similar drawings of other embodiments).

The cylindrical slider 40 is secured to the guide wire 30 to prevent relative rotational movement of the one with respect to the other, thereby assisting in providing rotational stability to the guide wire when the abrasive segment 54 of the drive shaft 50 is rotated at high speeds and engages tissue to be removed. If desired, the length of the keyway 18 can be limited to provide restrictions on the amount of advancement/retraction of the guide wire with respect to the catheter-this facilitates easy longitudinal alignment of the curved positioning portion 38 of the guide wire with the elongated aperture 16 in the catheter 10.

FIGS. 8 and 9 depict alternate configurations for the sides of the elongated aperture 16 in the catheter 10. In FIG. 8, the sides are generally parallel to one another; in FIG. 9 the sides are formed at an acute angle to one another.

FIGS. 11–21 depict yet another embodiment of the invention. In this embodiment, a plug 20 is disposed in the catheter lumen 14, preferably near the distal end 12 of the catheter 10. The plug 20 may be secured to the catheter by suitable adhesives or bonding techniques, including the use of one or more (preferably three or four) radially extending pins 21. Preferably the plug includes a central orifice 22 through which the guide wire 30 may pass. As depicted in FIG. 18 (a distal end view of the catheter), in this embodiment preferably the keyway 18 extends all the way to the distal end of the catheter to provide hydraulic relief as the cylindrical slider 40 moves longitudinally within the catheter.

FIG. 19 depicts a particular advantage of this embodiment of the invention. The solid lines in this figure depict the position of the intermediate segment of the drive shaft 50, including its abrasive segment 54, when the guide wire 30 is advanced distally to the point that the cylindrical slider 40 is stopped by the plug 20. Since the cylindrical slider 40 is securely attached to the guide wire 30, further distal advancement of the proximal portion of the guide wire 30 will cause further lateral deflection of the curved positioning portion 38 of the guide wire 30, thereby further urging the abrasive segment 54 of the drive shaft 50 toward the tissue being removed (as depicted by the phantom lines 54' of FIG. 19). Thus, this embodiment of the invention provides the physician with the ability to vary the effective lateral positioning of the abrasive segment of the drive shaft without having to exchange the device for one with a different guide wire.

FIGS. 20–21 illustrate in more detail an intermediate positioning portion 38 of an alternative embodiment of a guide wire 30. The curved portion preferably is constructed to be slightly more flexible than other portions of the guide wire, so that the wire preferentially bends in the curved positioning portion when the proximal portion of the guide wire is further advanced after the cylindrical slider 40 is stopped by the plug 20 in the catheter 10. Such increased flexibility can be provided by naking this portion of the guide wire of a smaller diameter, or by other suitable means.

While FIG. 20 exaggerates somewhat the difference in diameter, FIG. 21 depicts, roughly to scale, the degree of diameter reduction that has been found useful in providing the desired flexibility properties to the curved positioning portion of the guide wire. The wire, which has a normal diameter "D" in proximal and distal portions 43, tapers through a short length 44 of wire spanning a distance "L" to a smaller diameter "d" comprising the major portion 45 of the reduced diameter positioning portion. For wire having a normal diameter "D" of about 0.28 mm, length "L" may be approximately 1 mm, and smaller diameter "d" may be about 0.25 mm.

FIGS. 22–24 depict a slightly different embodiment of the invention. In this embodiment, the cylindrical slider 40 is provided with a radially extending peg 42 which is received in a complimentary slot 24 formed in the catheter 10. The peg/slot perform the same function as the key/keyway described above (i.e., rotationally aligning the curved positioning portion of the guide wire with the elongated aperture in the catheter), but also simultaneously provide limits on the longitudinal movement of the guide wire 30 with respect to the catheter 10 to effectively perform the function of the plug 20 described above (i.e., facilitating further lateral deflection of the curved positioning portion of the guide wire and abrasive segment of the drive shaft upon further advancement of the proximal portion of the guide wire after the peg 42 engages the distal end of the slot 24).

This embodiment of the invention includes another feature as well. To prevent undesired proximal movement of the drive shaft 50 with respect to the catheter 10 when the guide wire 30 is moved to its proximal position, the distal end portion of the drive shaft is provided with a thin sleeve 58 which engages a small shoulder 25 formed in a distal part of the distal section of the catheter lumen. This sleeve/shoulder engagement assures that the distal end of the drive shaft and, consequently, the drive shaft's abrasive segment, will not be withdrawn too far proximally. As depicted in FIGS. 23–24A, a distal stop 59 may also be provided to limit distal movement of the drive shaft 50 with respect to the catheter 10 when the guide wire 30 is moved distally with respect to the catheter. The distal stop may be made from any suitable material, including plastics or metals. FIG. 24 shows in perspective view a distal stop 59, which may be made of a suitable plastic and which may be ultrasonically or otherwise welded (or secured by any other suitable means) at the desired location within the catheter lumen. FIG. 24A depicts a modified embodiment of such a distal stop 59, being formed of a split ring having a size providing an interference fit (i.e., having a normal, relaxed outer diameter slightly larger than the internal diameter of the catheter). Other equivalent mechanisms may similarly be employed to limit the proximal and distal movement of the drive shaft as the guide wire is moved proximally and distally with respect to the catheter.

FIGS. 25–26 illustrate another variation of the increased flexibility/reduced-diameter guide wire. In this embodiment, the proximal portion 43' of the guide wire 30' has a constant, larger diameter "D", which decreases through a tapered portion 44' to a smaller diameter "d" portion 45' (including both the intermediate curved positioning portion 38' and the distal portion of the guide wire). Again, the degree of actual taper is somewhat exaggerated in FIGS. 25–26 for illustrative purposes; the amount of actual taper would be similar to that depicted in FIG. 21. In this embodiment the cylindrical member 40' is rigidly affixed to both the guide wire 30' and the distal section of the catheter 10 so that the distal portion of the guide wire 30' is not movable with respect to the catheter. The intermediate curved positioning portion 38' of the guide wire 30' is formed with just a slight curve-sufficiently gentle that in its at-rest position (depicted in FIG. 25) the drive shaft's abrasive segment does not protrude out of the elongated aperture 16 in the catheter 10, but when the proximal portion of the guide wire 30' is advanced distally, the intermediate curved positioning portion 38' of the guide wire 30' deflects laterally to urge the drive shaft's abrasive segment laterally out through the catheter aperture 16 to engage tissue to be removed from a bodily passageway or cavity.

The above-described embodiments of the atherectomy device of the invention are all depicted as utilizing a single wire performing the functions of a guide wire and of a wire laterally positioning the abrasive segment of the drive shaft. The invention may also be employed utilizing a positioning wire separate from the guide wire. FIGS. 27–49 illustrate such two wire systems. In these drawings, most of the reference numbers (all of which are in the 100 series of numbers) refer to the corresponding elements of FIGS. 1–26, with the reference numbers being 100 higher (e.g., element 116 of FIG. 27 corresponds to element 16 of FIGS. 1–26).

The embodiment depicted in FIGS. 27–31 is essentially similar to the embodiment of FIGS. 1–4. An elongated catheter 111 has a central lumen 114, in which is disposed a flexible drive shaft 150. The drive shaft preferably is of the type made from helically wound wire, the wire turns 152 being depicted in FIGS. 27 and 28 but being omitted from many of the other drawings for the sake of clarity. The catheter 111 includes, in addition to the primary lumen 114 housing the drive shaft 150, a separate lumen 115 for a conventional guide wire 132, which terminates distally in a conventional coiled distal tip portion 136.

A separate positioning wire 134 is provided for controlling the positioning of the abrasive segment 154 of the drive shaft 150. In the embodiment depicted in FIGS. 27–31, the positioning wire 134 includes three portions, a generally straight proximal portion, a generally straight distal portion, and an intermediate portion which has a predetermined curved shape. As can be seen by comparing FIGS. 27 and 29 with FIGS. 28 and 31, longitudinal movement of the positioning wire 134 provides control over the lateral position of the abrasive segment 154 of the drive shaft 150. When the positioning wire 134 is retracted with respect to the catheter 111 and drive shaft 50 (see FIGS. 28 and 31), the intermediate curved portion of the positioning wire 134 is contained by the lumen 14 of the catheter 111, thus retaining the drive shaft 150 generally within the catheter 111. When the curved intermediate portion of the positioning wire 134 is advanced to where it is aligned with the elongated aperture 116 of the catheter 111, however, the curved portion of the positioning wire 134 urges the corresponding segment of the flexible drive shaft 150 out through the elongated aperture 116 and into engagement with the tissue desired to be removed. Notice that the movement of the positioning wire 134 depicted by comparing FIGS. 29 and 31 is only equal to about one-half the length of the elongated aperture 116 in the catheter 111—the apex of the curved portion of the positioning wire in FIG. 31 is located just slightly proximal to the proximal end of the catheter's elongated aperture 116, thus giving the drive shaft 150 a slight serpentine configuration in FIG. 31.

Thus, as with the embodiment of FIGS. 1–4, withdrawing the positioning wire 134 so that the proximal half of the curved intermediate portion of the positioning wire is contained within the catheter lumen causes the abrasive segment of the drive shaft to lay substantially within the catheter lumen (though in a slightly serpentine shape), and advancement of the positioning wire to align the positioning wire's curved intermediate portion with the elongated aperture of the catheter permits this curved portion to urge the abrasive segment of the drive shaft laterally out against the tissue to be abraded.

FIGS. 32–35 correspond generally to FIGS. 5–10. In this embodiment, the positioning wire includes alignment means for rotationally aligning the curved intermediate positioning portion of the positioning wire 134 with the catheter's elongated aperture 116. Although means for accomplishing this rotational alignment could be provided in several ways, in a preferred embodiment the alignment means comprises a key and keyway, one of which is associated with the positioning wire 134 and the other of which is associated with the catheter 111, thereby rotationally aligning the positioning wire with the catheter. FIGS. 32–35 depict a cylindrical slider 140 having an integral key 141 received in a complimentary keyway 118 formed in the wall of the catheter 111. This configuration could be reversed, but the configuration depicted provides for relatively easier manufacturing.

The cylindrical slider 140 is secured to the positioning wire 134 to prevent relative rotational movement of the one with respect to the other, thereby assisting in providing rotational stability to the positioning wire when the abrasive segment 154 of the drive shaft 150 is rotated at high speeds and engages tissue to be removed. If desired, the length of the keyway 118 can be limited to provide restrictions on the amount of advancement/retraction of the positioning wire with respect to the catheter—this facilitates easy longitudinal alignment of the curved positioning portion 138 of the positioning wire with the elongated aperture 116 in the catheter 111.

FIGS. 34 and 35 depict alternate configurations for the sides of the elongated aperture 116 in the catheter 111. In FIG. 34, the sides are generally parallel to one another; in FIG. 35 the sides are formed at an acute angle to one another.

FIGS. 36–45 correspond generally to FIGS. 11–21. In this embodiment, a plug 120 is disposed in the catheter lumen 114, preferably near the distal end 112 of the catheter 111. The plug 120 may be secured to the catheter by suitable adhesives or bonding techniques, including the use of one or more (preferably three or four) radially extending pins 121. Unlike the embodiment of FIGS. 11–21, the plug need not include a central orifice for the guide wire, since the guide wire 132 in this embodiment is disposed in a separate lumen 115. As depicted in FIG. 43, (a distal end view of the catheter), preferably the keyway 118 extends all the way to the distal end of the catheter to provide hydraulic relief as the cylindrical slider 140 with its key 141 moves longitudinally within the catheter 111.

FIGS. 36 and 38 depict a particular advantage of this embodiment of the invention. The solid lines in these figures depict the position of the intermediate segment of the drive shaft 150, including its abrasive segment 154, when the positioning wire 134 is advanced distally to the point that the cylindrical slider 140 is stopped by the plug 120. Since the cylindrical slider 140 is securely attached to the positioning wire 134, further distal advancement of the proximal portion of the positioning wire 134 will cause further lateral deflection of the curved positioning portion 138 of the positioning wire 134, thereby further urging the abrasive segment 154 of the drive shaft 150 toward the tissue being removed (as depicted by the phantom lines 154' of FIGS. 36 and 38). Thus, this embodiment of the invention provides the physician with the ability to vary the effective lateral positioning of the abrasive segment of the drive shaft without having to exchange the device for one with a different positioning wire.

Figure 44:
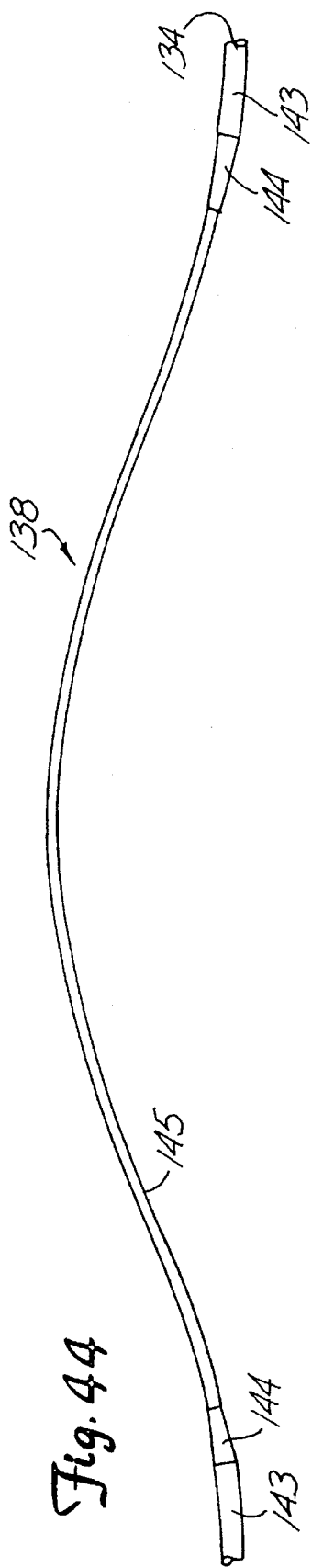
FIG. 44 shows an intermediate portion of an alternate embodiment of a guide wire which can be used in the atherectomy device of FIGS. 37–43.
Figure 45:
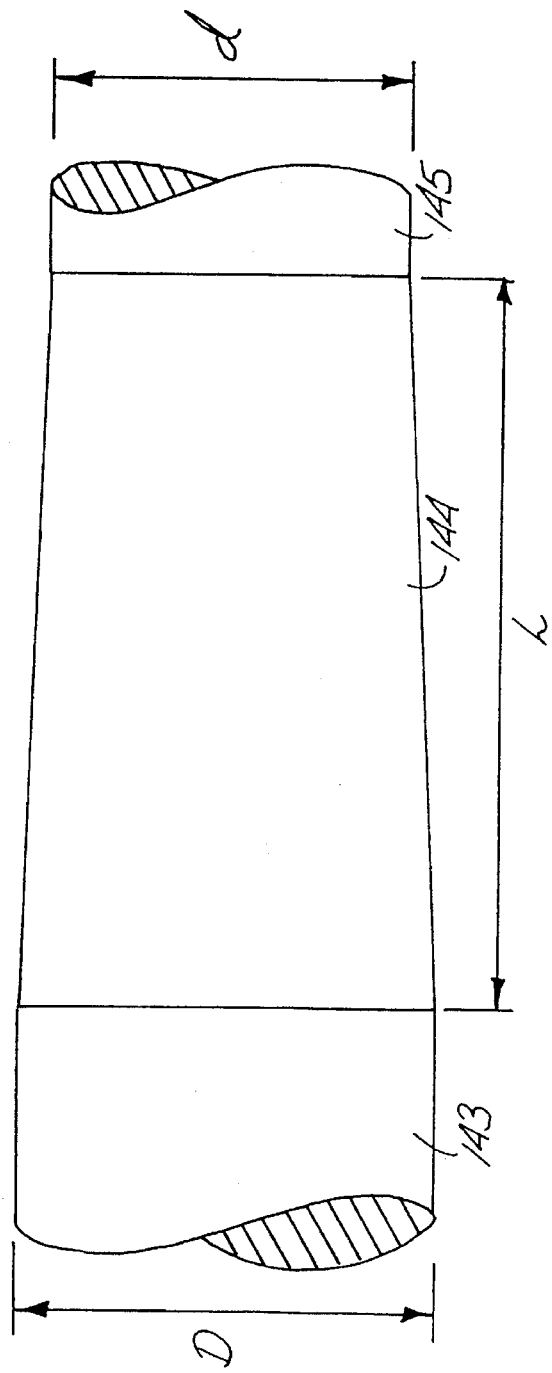
FIG. 45 is an enlarged detail drawing of a portion of the guide wire of FIG. 44.

FIGS. 44–45 illustrate in more detail an intermediate positioning portion 138 of an alternate embodiment of a positioning wire 134. The curved portion preferably is constructed to be slightly more flexible than other portions of the positioning wire, so that the wire preferentially bends in the curved positioning portion when the proximal portion of the positioning wire is further advanced after the cylindrical slider is stopped by the plug 120 in the catheter 111. Such increased flexibility can be provided by making this portion of the positioning wire of a smaller diameter, or by other suitable means. While FIG. 44 exaggerates somewhat the difference in diameter, FIG. 45 depicts, roughly to scale, the degree of diameter reduction that has been found useful in providing the desired flexibility properties to the curved positioning portion 138 of the positioning wire 134. The wire, which has a normal diameter "D" in proximal and distal portions 143, tapers through a short length 144 of wire spanning a distance "L" to a smaller diameter "d" comprising the major potion 145 of the reduced diameter positioning portion. For wire having a normal diameter "D" of about 0.28 mm, length "L" may be approximately 1 mm, and smaller diameter "d" may be about 0.25 mm.

FIGS. 46–48 depict an embodiment that corresponds generally to FIGS. 22–25. In this embodiment, the cylindrical slider 140 is provided with a radially extending peg 142 which is received in a complimentary slot 124 formed in the catheter 111. The peg/slot perform the same function as the key/keyway described above (i.e., rotationally aligning the curved positioning portion of the positioning wire 134 with the elongated aperture 116 in the catheter 111 ), but also simultaneously provide limits on the longitudinal movement of the positioning wire 134 with respect to the catheter 111 to effectively perform the function of the plug 120 described above (i.e., facilitating further lateral deflection of the curved positioning portion of the positioning wire and abrasive segment of the drive shaft upon further advancement of the proximal portion of the positioning wire after the peg 142 engages the distal end of the slot 124).

This embodiment of the invention includes another feature as well. To prevent excessive undesired proximal movement of the drive shaft 150 with respect to the catheter 111 when the positioning wire 134 is moved to its proximal position, the distal end portion of the drive shaft 150 is provided with a thin sleeve 158 which engages a small shoulder 125 formed in a distal part of the distal section of the catheter lumen. This sleeve/shoulder engagement assures that the distal end of the drive shaft and, consequently, the drive shaft's abrasive segment, will not be withdrawn too far proximally. FIG. 47 depicts a curved and tapered intermediate positioning portion 138 of the positioning wire 134 that is similar to the intermediate portion 138 of the positioning wire 134 shown in FIG. 44.

FIG. 49 illustrates another variation of the increased flexibility/reduced-diameter positioning wire. In this embodiment, the proximal portion 143' of the positioning wire 134' has a constant, larger diameter which decreases through a tapered portion 144' to a smaller diameter portion 145' (including both the intermediate curved positioning portion 138' and the distal portion of the positioning wire). In this embodiment the cylindrical member 140' is rigidly affixed to both the positioning wire 134' and the distal section of the catheter 111 so that the distal portion of the positioning wire 134' is not movable with respect to the catheter. The intermediate curved positioning portion 138' of the positioning wire 134' is formed with just a slight curve—sufficiently gentle that in its at-rest position the drive shaft's abrasive segment does not protrude out of the elongated aperture 116 in the catheter 111, but when the proximal portion of the positioning wire 134' is advanced distally, the intermediate curved positioning portion 138' of the positioning wire 134' deflects laterally to urge the drive shaft's abrasive segment laterally out through the catheter aperture 116 to engage tissue to be removed from a bodily passageway or cavity.

The operation and function of the abrasive drive shaft device of the invention in removing an atherosclerotic lesion or atheroma from an artery is set forth below, being described in reference to the embodiments of FIGS. 27–49 (i.e., the embodiments having a positioning wire 134 separate from the guide wire 132).

The device of the invention is particularly useful in removing asymmetrical stenotic lesions. Although the device will work just as well with symmetrical stenotic lesions or only mildly asymmetrical stenotic lesions, the advantages of the invention are best realized with respect to an atherosclerotic lesion that is located predominantly on one side of the arterial wall.

Commercially available angioplasty equipment (e.g., arterial puncture needles, arterial dilators, sheath introducers and guide catheters) and routine angioplasty techniques are used to appropriately position the abrasive drive shaft device in the arteries of interest.

The guide wire is advanced through the artery to a position where its distal tip is located distally of the stenosis to be treated. The catheter, including the positioning wire and the flexible drive shaft with its abrasive segment, is advanced over the shaft of the guide wire to a position locating the abrasive segment adjacent to the stenotic lesion. Prior to advancement of the catheter through the artery, the proximal half of the curved positioning portion of the positioning wire is withdrawn proximally of the aperture in the catheter. This temporarily straightens (not completely, but substantially) the intermediate positioning portion of the positioning wire, holding the abrasive segment of the drive shaft substantially within the lumen of the catheter, and thereby giving the entire device a very low profile. Such a low profile of the device enables the device to be advanced into relatively tight arterial stenoses.

When in position, the positioning wire is advanced distally until its curved positioning portion extends laterally out of the catheter's elongated aperture, regaining (at least partially) its predetermined shape and urging the abrasive segment of the drive shaft laterally against tissue to be removed. Since the abrasive segment is engaged against the atherosclerotic lesion, the positioning portion of the positioning wire will not have entirely regained its predetermined shape, being limited by the presence of the atherosclerotic plaque.

At this point, the positioning wire, the catheter and the flexible drive shaft (with its abrasive segment) can be advanced distally and retracted proximally as a unit while the drive shaft is being rotated at relatively high speed (typically in the range of about 30,000 RPM to about 600,000 RPM, or even more, depending only on the physical dimensions and capabilities of the turbine/motor and flexible drive shaft) to selectively remove a portion of the stenotic lesion.

A combination of the above-described longitudinal movements of the catheter, together with rotation of the catheter within the artery, may be utilized to remove stenotic tissue from only a sector of the artery or from the entire circumference of the artery.

If the curved positioning portion of the positioning wire entirely regains its predetermined shape before the stenosis is sufficiently opened, the atherectomy device may be exchanged over the guide wire for an atherectomy device having a positioning wire with a greater lateral deflection capability.

Alternately, if the atherectomy device is one of the embodiments described above having a plug in the distal portion of the catheter (or an equivalent functioning mechanism for stopping distal movement of the distal portion of the positioning wire), then further distal advancement of the proximal portion of the positioning wire will further deflect the positioning wire's intermediate curved positioning portion, thereby further urging the abrasive segment of the drive shaft laterally against the stenotic tissue to be removed.

When a sufficient amount of the lesion has been removed, the intermediate positioning portion can again be withdrawn into the catheter to again draw the abrasive segment substantially within the lumen of the catheter, and the entire device, including the guide wire, can be withdrawn.

As can be seen from the above discussion in reference to the drawings, during the entire procedure the abrasive segment never need come into contact with the wall of the artery across from the atherosclerotic lesion. Rather, the device provides directional control over the lateral location of the abrasive segment within the artery, permitting contact of the abrasive segment substantially only with stenotic tissue.

Lumens of a very large arteries can be re-opened to their original diameter (e.g., 5–7 mm in the iliac and femoral arteries) with use of a comparatively small diameter abrasive segment (e.g., about 1 mm in diameter or less), a capability not easily obtainable with the Auth-type device, since it may require performing a cut-down on the common femoral artery in order to introduce the larger abrasive burrs (e.g., over 3 or 4 mm in diameter) of the Auth-type device. In some cases this would be entirely impossible, as the normal diameter of the artery through which the drive shaft with its abrasive burr preferably is introduced may only be, e.g., 3–4 mm or less. An example of this would be using the brachial artery approach (having a diameter of about 3–4 mm or less) to reach the iliac or femoral artery (having a diameter of 5–7 mm). Moreover, an atherectomy device of the invention designed for opening such large arteries may be introduced through arteries having an inner diameter as small as 2 mm or even less.

In the embodiments of the invention utilizing a single wire as the guide wire and positioning wire, the above method of use is simply modified to account for the presence of a single wire. In most cases, this means that the entire unit will be advanced, as a unit, into the artery (or other bodily passageway), but most of the other operations will be substantially similar to the procedure described above.

The atherectomy device of the invention may also be provided with ultrasound imaging capability. FIG. 50 depicts an embodiment having several ultrasound transducers 70 mounted between successive turns 73 of a tri-filar outer layer of a two-layer helically wound drive shaft 50. Preferably, as shown in FIG. 50, the transducers are aligned along a common plane oriented perpendicularly to the longitudinal axis of the drive shaft 50. Electrical leads 71 extend proximally from the transducers 70, being helically wound in the gap between the successive turns of the drive shaft 50.

Figure 51:
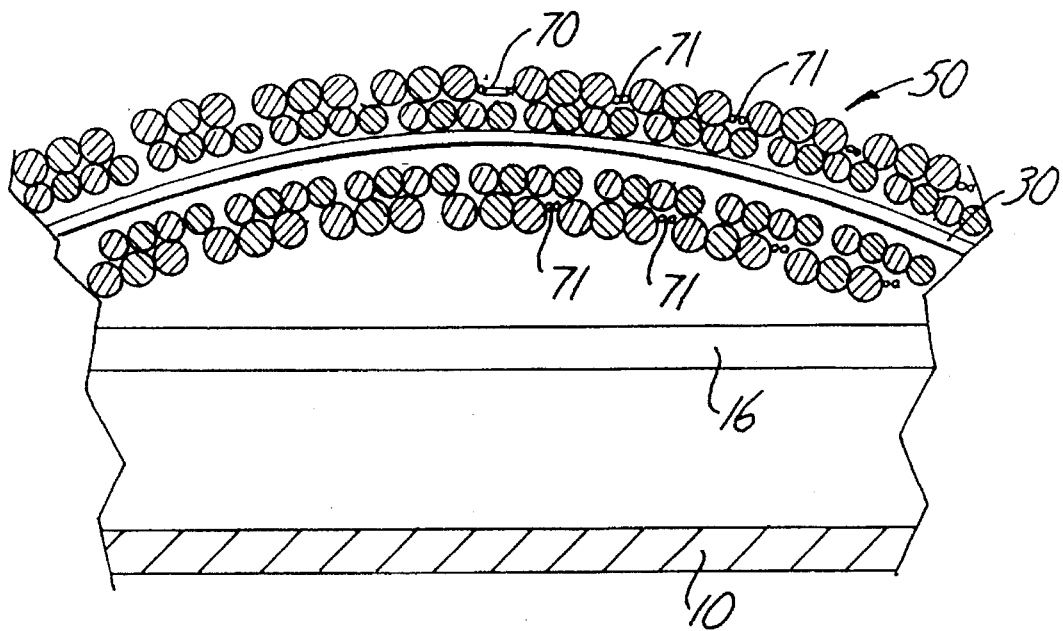
FIG. 51 is a longitudinal cross-sectional view of a two-layer drive shaft carrying an ultrasonic transducer, the drive shaft shown extending out through an elongated aperture in a catheter.
Figure 52:
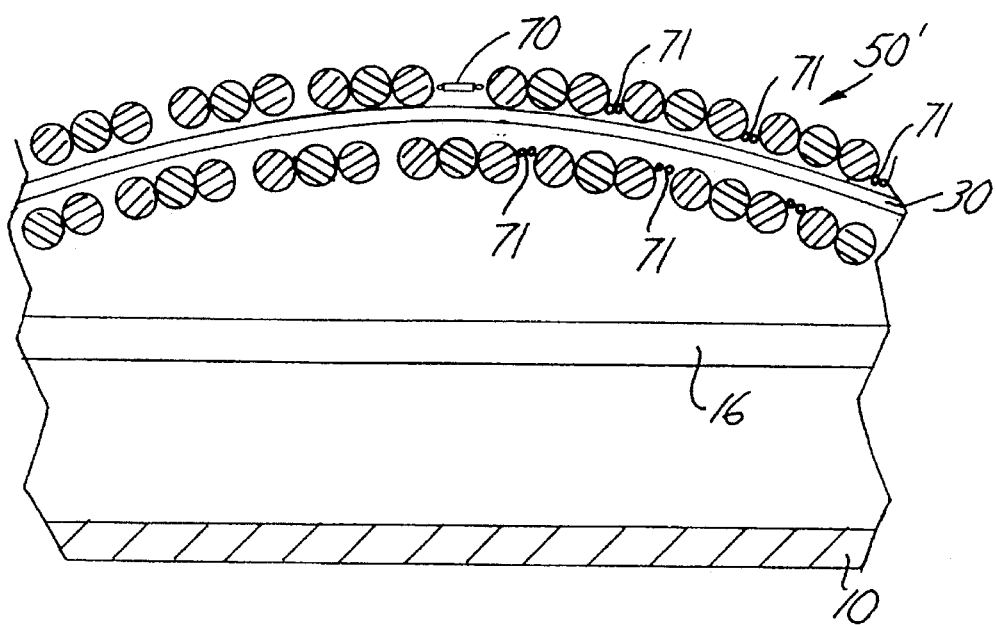
FIG. 52 is a longitudinal cross-sectional view of a single layer drive shaft carrying an ultrasonic transducer, the drive shaft shown extending out through an elongated aperture in a catheter.
Figure 53:
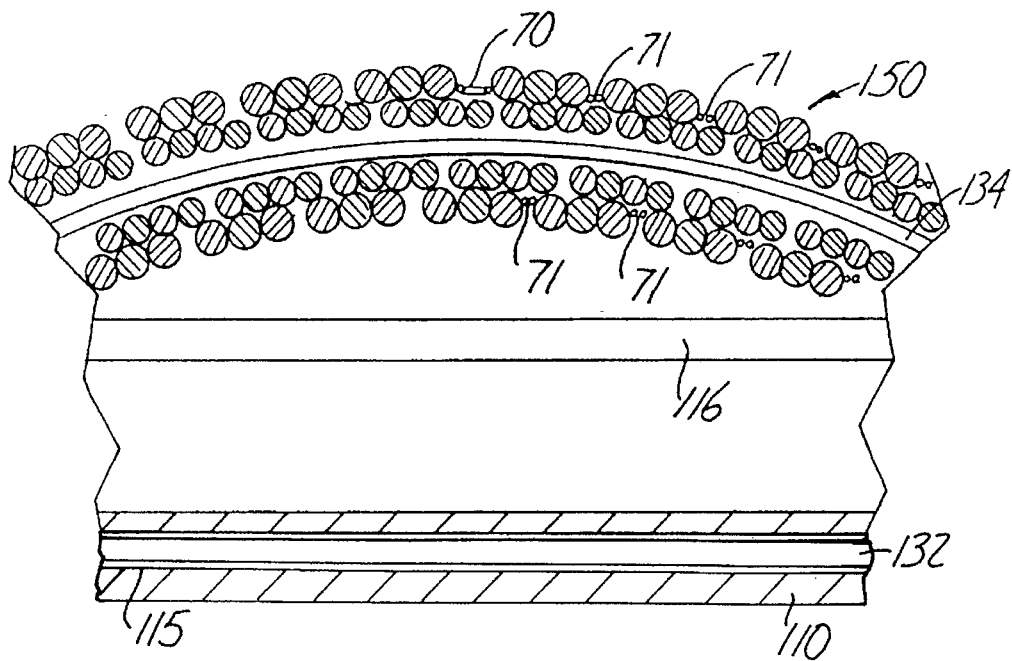
FIG. 53 is a longitudinal cross-sectional view of a two-layer drive shaft carrying an ultrasonic transducer, the drive shaft shown extending out through an elongated aperture in a dual lumen catheter.
Figure 54:
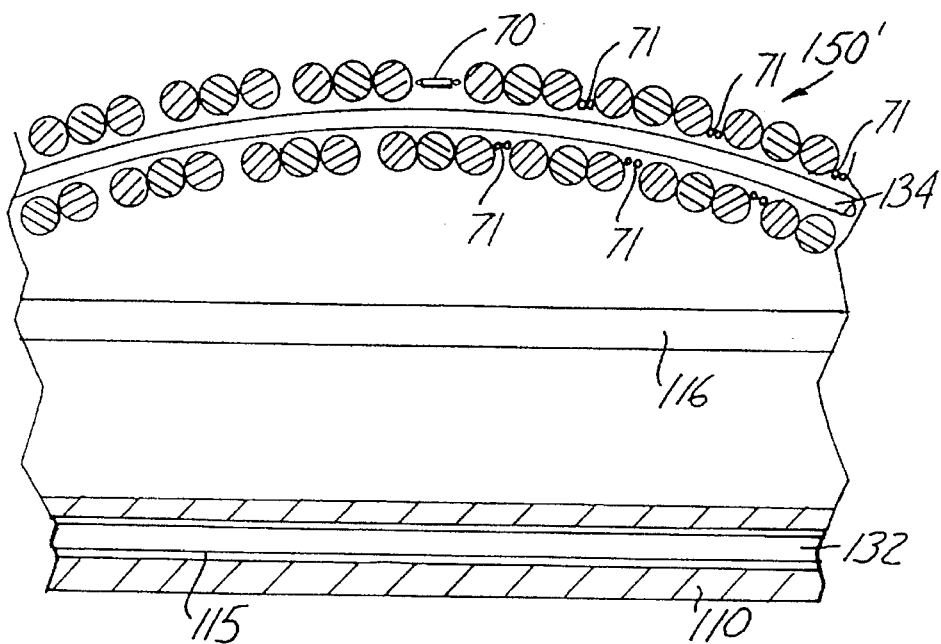
FIG. 54 is a longitudinal cross-sectional view of a single layer drive shaft carrying an ultrasonic transducer, the drive shaft shown extending out through an elongated aperture in a dual lumen catheter.

FIG. 51 is a longitudinal cross-sectional view of a two-layer drive shaft 50 carrying an ultrasonic transducer 70, the electrical leads 71 attached to the transducer extending proximally and being helically wound in the gap between the successive turns of the drive shaft 50. In this drawing the drive shaft is shown extending out through an elongated aperture 16 in the catheter 10. FIG. 52 is similar to FIG. 51, but depicts a single layer, tri-filar drive shaft 50'. FIGS. 53–54 depict use of ultrasound transducers 70 in a two-wire system employing a dual-lumen catheter 110, the additional lumen 115 being provided to accommodate a guide wire 132 independent from the positioning wire 134 around which the drive shaft 150 (150') is rotated.

Single or two-layer, multi-friar drive shafts of the types described above are commercially available from Lake Region Manufacturing Co. of Chaska, Minn. Two layer drive shafts may be manufactured with an interference fit between the two layers as described in e Region Manufacturing's U.S. Pat. No. 5,165,421. The transducers 70 may be secured to the drive shaft by silicone rubber, sonolucent plastics, adhesives or other conventional means (not shown in the drawings for purposes of clarity).

Figure 55:
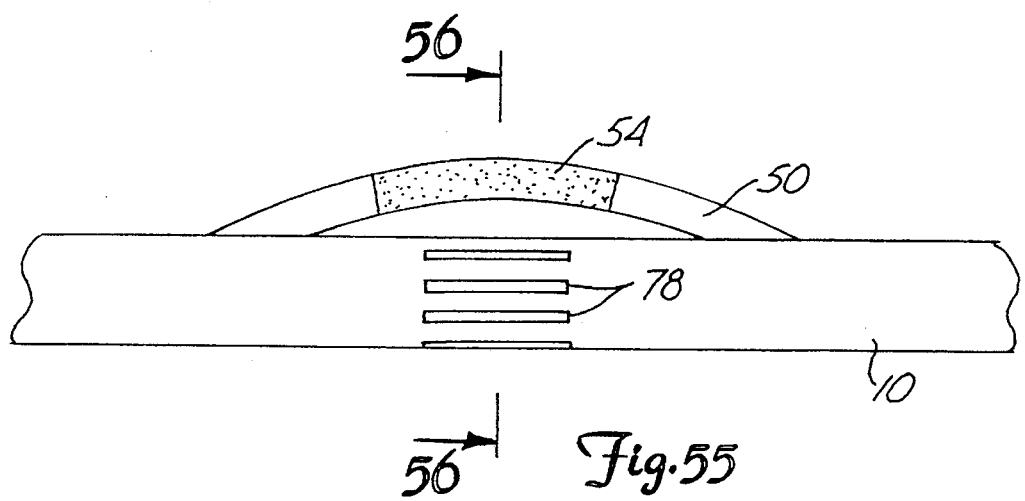
FIG. 55 is a partially broken-away view of another embodiment of the invention containing ultrasound imaging capability.
Figure 56:
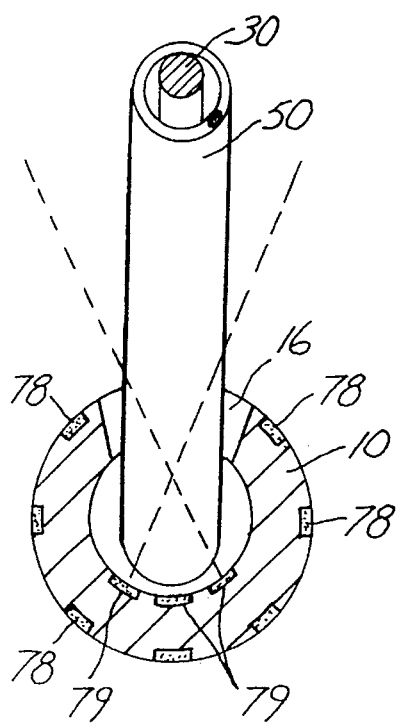
FIG. 56 is a cross-sectional view of FIG. 52 taken along lines 52—52 thereof.
Figure 57:
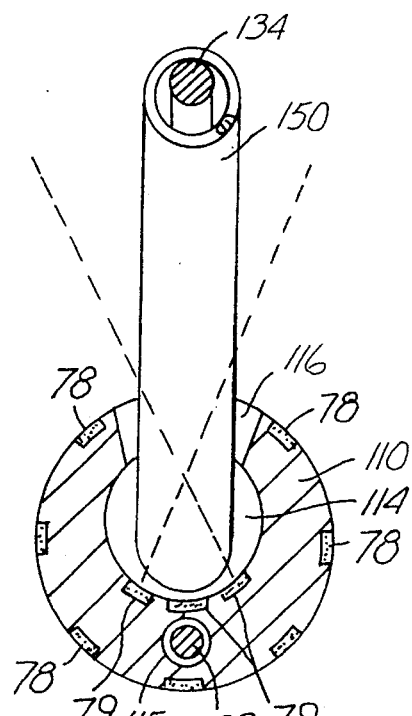
FIG. 57 is a cross-sectional view of an embodiment similar to FIG. 56 having a dual lumen catheter.

FIGS. 55–56 depict another embodiment having inner and/or outer ultrasound transducers 78 and 79 carried by the catheter 10—the outer transducers 78 are oriented to image radially outwardly from the catheter's outer surface, and the inner transducers 79 are oriented to image radially inwardly from the surface of the catheter drive shaft lumen, with their ultrasonic beams passing out of the catheter through the catheter aperture 16. FIG. 57 is a cross-sectional view of an embodiment similar to the embodiment of FIGS. 55–56 having a dual lumen catheter 110, the inner ultrasound transducers 79 being positioned to image from the surface of the catheter drive shaft lumen 114.

Ultrasound transducer arrangements other than those depicted in FIGS. 50–57 may similarly be provided to enable imaging of the tissue aligned with the abrasive segment of the drive shaft of atherectomy devices utilizing one or two wire systems. Ultrasound transducers usable in connection with the invention may be of the type utilized by, e.g., Endosonics Corporation of Sunnyvale, Calif.

While a preferred embodiment of the present invention has been described, it should be understood that various changes, adaptations and modifications may be made therein without departing from the spirit of the invention and the scope of the appended claims.

What is claimed is:

1. An atherectomy device for removing tissue from a bodily passageway or cavity, comprising:

a rotational atherectomy apparatus having a flexible, elongated drive shaft with a proximal segment, an intermediate segment, and a distal segment, a portion of the intermediate segment being coated with an abrasive material to define an abrasive segment of the drive shaft, the drive shaft further including a central lumen for receipt of a guide wire therein, around which the drive shaft may be rotated;

a guide wire having proximal, intermediate and distal portions, the proximal portion being generally straight, the intermediate portion having a predetermined curved positioning portion such that when the abrasive segment of the drive shaft is located along the curved positioning portion, such curved portion urges the abrasive segment laterally; and a catheter having side walls defining a lumen sized to receive the drive shaft therein, the catheter having proximal, intermediate and distal sections, the intermediate section having an elongated aperture in the side wall, the aperture having a width permitting the abrasive segment of the drive shaft to extend therethrough so that when the abrasive segment of the drive shaft and the curved positioning portion of the guide wire are both aligned with the aperture in the side wall of the catheter, such curved positioning portion urges the abrasive segment laterally out through the catheter aperture to engage tissue to be removed from a bodily passageway or cavity.

2. The atherectomy device of claim 1 wherein the guide wire is movable from a first position wherein the guide wire's curved positioning portion is generally aligned with the elongated aperture to urge the abrasive segment of the drive shaft laterally out through the elongated aperture, and a second position where at least about half of the guide wire's curved positioning portion is located proximally to the catheter's elongated aperture.

3. The atherectomy device of claim 1 wherein the guide wire is movable from a first position wherein the guide wire's curved positioning portion is generally aligned with the elongated aperture to urge the abrasive segment of the drive shaft laterally out through the elongated aperture, and a second position where at least part of the guide wire's curved positioning portion is located proximally to the catheter's elongated aperture, so that the abrasive segment of the drive shaft does not protrude laterally out of the elongated aperture.

4. The atherectomy device of claim 1 wherein the guide wire is movable from a first position wherein the guide wire's curved positioning portion is generally aligned with the elongated aperture to urge the abrasive segment of the drive shaft laterally out through the elongated aperture, and a second position where at least about half of the guide wire's curved positioning portion is located either distally or proximally to the catheter's elongated aperture.

5. The atherectomy device of claim 1 wherein the guide wire is movable from a first position wherein the guide wire's curved positioning portion is generally aligned with the elongated aperture to urge the abrasive segment of the drive shaft laterally out through the elongated aperture, and a second position where at least part of the guide wire's curved positioning portion is located either distally or proximally to the catheter's elongated aperture, so that the abrasive segment of the drive shaft does not protrude laterally out of the elongated aperture.

6. The atherectomy device of claim 1 wherein the guide wire includes alignment means for rotationally aligning the guide wire's curved positioning portion with the catheter's elongated aperture.

7. The atherectomy device of claim 6 wherein the alignment means comprises a key and keyway, one of which is associated with the guide wire and the other of which is associated with the catheter, thereby rotationally aligning the guide wire with the catheter.

8. The atherectomy device of claim 7 wherein the key is carried by a slider secured to the distal portion of the guide wire, and the keyway is formed in a side wall of the catheter.

9. The atherectomy device of claim 8 wherein the slider is generally cylindrical in shape.

10. The atherectomy device of claim 1 further comprising a slider secured to the distal portion of the guide wire.

11. The atherectomy device of claim 10 wherein the slider is generally cylindrical in shape.

12. The atherectomy device of claim 1 wherein the distal section of the catheter includes blocking means for stopping distal advancement of the distal portion of the guide wire so that when the intermediate portion of the guide wire and the abrasive segment of the drive shaft are both aligned with the aperture in the side wall of the catheter, then further advancement of the proximal portion of the guide wire will cause further lateral deflection of the intermediate portion of the guide wire, thereby urging the abrasive segment of the drive shaft further laterally out through the catheter aperture to engage tissue to be removed from a bodily passageway or cavity.

13. The atherectomy device of claim 12 wherein the intermediate portion of the guide wire has greater flexibility than the proximal portion of the guide wire.

14. The atherectomy device of claim 13 wherein the intermediate portion of the guide wire is of a diameter that is less than the diameter of the proximal portion of the guide wire.

15. The atherectomy device of claim 12 wherein the blocking means comprises a plug in the catheter lumen located distally of the elongated aperture.

16. The atherectomy device of claim 12 further comprising a slider secured to the distal portion of the guide wire, the slider being engagable against the plug in the catheter lumen to prevent distal movement of the slider past the plug.

17. The atherectomy device of claim 16 wherein the slider is generally cylindrical in shape.

18. The atherectomy device of claim 16 wherein the slider includes a key, and the catheter has a complementary keyway for rotationally aligning the intermediate curved positioning portion of the guide wire with the elongated aperture of the catheter.

19. The atherectomy device of claim 12 wherein the blocking means comprises a complementary peg and longitudinal slot, one of which is associated with the catheter and the other of which is associated with the guide wire, the longitudinal slot having a distal end so that engagement of the peg with the end of the slot stops distal advancement of the distal portion of the guide wire.

20. The atherectomy device of claim 19 wherein the longitudinal slot is formed in the catheter side wall, and the peg extends radially outwardly from a slider which is secured to the guide wire and is slidably disposed within the catheter lumen.

21. The atherectomy device of claim 20 wherein the slider is generally cylindrical in shape.

22. The atherectomy device of claim 1 further comprising a generally cylindrical slider secured to the distal portion of the guide wire, a peg extending generally radially outwardly from the slider into a complementary longitudinal slot formed in the catheter side wall, the peg and slot functioning as a key and keyway for rotationally aligning the intermediate curved positioning portion of the guide wire with the elongated aperture of the catheter, the slot having a distal end against which the peg may abut, the peg and complementary longitudinal slot being positioned relative to one another so that when the intermediate portion of the guide wire and the abrasive segment of the drive shaft are both aligned with the aperture in the side wall of the catheter, the peg will abut the distal end of the longitudinal slot and further advancement of the proximal portion of the guide wire will then cause further lateral deflection of the intermediate portion of the guide wire, thereby urging the abrasive segment of the drive shaft further laterally out through the catheter aperture to engage tissue to be removed from a bodily passageway or cavity.

23. The atherectomy device of claim 22 wherein the distal end portion of the drive shaft is provided with a sleeve which is engagable with a shoulder formed in the distal section of the catheter lumen to stop proximal movement of the distal end of the drive shaft beyond the shoulder when the guide wire is being withdrawn proximally with respect to the catheter.

24. The atherectomy device of claim 23 wherein the shoulder is formed in the distal section of the catheter by making a distal part of such distal section of the catheter with an inner diameter which is larger than the inner diameter of the remaining part of the distal section of the catheter.

25. The atherectomy device of claim 1 wherein the distal end portion of the drive shaft is provided with a sleeve which is engagable with a shoulder formed in the distal section of the catheter lumen to stop proximal movement of the distal end of the drive shaft beyond the shoulder when the guide wire is being withdrawn proximally with respect to the catheter.

26. The atherectomy device of claim 25 wherein the shoulder is formed in the distal section of the catheter by making a distal part of such distal section of the catheter with an inner diameter which is larger than the inner diameter of the remaining part of the distal section of the catheter.

27. An atherectomy device for removing tissue from a bodily passageway or cavity, comprising:

a rotational atherectomy apparatus having a flexible, elongated drive shaft with a proximal segment, an intermediate segment, and a distal segment, a portion of the intermediate segment being coated with an abrasive material to define an abrasive segment of the drive shaft, the drive shaft further including a central lumen for receipt of a guide wire therein, around which the drive shaft may be rotated;

a guide wire having proximal, intermediate and distal portions, the proximal portion being generally straight, the intermediate portion having a slight predetermined curved positioning portion to urge the abrasive segment slightly laterally;

a catheter having side walls defining a lumen sized to receive the drive shaft therein, the catheter having proximal, intermediate and distal sections, the intermediate section having an elongated aperture in the side wall, the aperture having a width permitting the abrasive segment of the drive shaft to extend therethrough;

the distal section of the catheter including means for securing the distal portion of the guide wire with respect to the catheter in a position such that the curved positioning portion of the guide wire is aligned with the aperture in the catheter side wall, so that when the proximal portion of the guide wire is advanced, then the curved positioning portion of the guide wire becomes further deflected laterally, thereby also urging the abrasive segment of the drive shaft further laterally and out through the catheter aperture to engage tissue to be removed from a bodily passageway or cavity.

28. The atherectomy device of claim 27 wherein the lateral deflection of the curve of the predetermined curved positioning portion of the guide wire is small enough that the abrasive segment of the drive shaft normally does not protrude out of the catheter's elongated aperture until the proximal portion of the guide wire is advanced to cause further lateral deflection of the curved positioning portion of the guide wire.

29. The atherectomy device of claim 27 wherein the means for securing the distal portion of the guide wire with respect to the catheter comprises a plug in the catheter lumen located distally of the elongated aperture.

30. The atherectomy device of claim 27 wherein the intermediate portion of the guide wire has greater flexibility than the proximal portion of the guide wire.

31. The atherectomy device of claim 27 wherein the intermediate portion of the guide wire is of a diameter that is less than the diameter of the proximal portion of the guide wire.

32. An atherectomy device for removing tissue from a bodily passageway or cavity, comprising:

a rotational atherectomy apparatus having a flexible, elongated drive shaft with a proximal segment, an intermediate segment, and a distal segment, a portion of the intermediate segment being coated with an abrasive material to define an abrasive segment of the drive shaft, the drive shaft further including a central lumen for receipt of a positioning wire therein, around which the drive shaft may be rotated;

a positioning wire having proximal, intermediate and distal portions, the proximal portion being generally straight, the intermediate portion having a predetermined curved positioning portion such that when the abrasive segment of the drive shaft is located along the curved positioning portion, such curved portion urges the abrasive segment laterally; and a catheter having walls defining a pair of lumens, one being a guide wire lumen sized to receive a guide wire therein, and the other being a drive shaft lumen sized to receive the drive shaft therein, the catheter having proximal, intermediate and distal sections, the intermediate section having an elongated aperture in the wall defining the drive shaft lumen, the aperture having a width permitting the abrasive segment of the drive shaft to extend therethrough so that when the abrasive segment of the drive shaft and the curved positioning portion of the positioning wire are both aligned with the aperture in the wall of the catheter, such curved positioning portion urges the abrasive segment laterally out through the catheter aperture to engage tissue to be removed from a bodily passageway or cavity.

33. The atherectomy device of claim 32 wherein the positioning wire is movable from a first position wherein the positioning wire's curved positioning portion is generally aligned with the elongated aperture to urge the abrasive segment of the drive shaft laterally out through the elongated aperture, and a second position where at least about half of the positioning wire's curved positioning portion is located proximally to the catheter's elongated aperture.

34. The atherectomy device of claim 32 wherein the positioning wire is movable from a first position wherein the positioning wire's curved positioning portion is generally aligned with the elongated aperture to urge the abrasive segment of the drive shaft laterally out through the elongated aperture, and a second position where at least part of the positioning wire's curved positioning portion is located proximally to the catheter's elongated aperture, so that the abrasive segment of the drive shaft does not protrude laterally out of the elongated aperture.

35. The atherectomy device of claim 32 wherein the positioning wire is movable from a first position wherein the positioning wire's curved positioning portion is generally aligned with the elongated aperture to urge the abrasive segment of the drive shaft laterally out through the elongated aperture, and a second position where at least about half of the positioning wire's curved positioning portion is located either distally or proximally to the catheter's elongated aperture.

36. The atherectomy device of claim 32 wherein the positioning wire is movable from a first position wherein the positioning wire's curved positioning portion is generally aligned with the elongated aperture to urge the abrasive segment of the drive shaft laterally out through the elongated aperture, and a second position where at least part of the positioning wire's curved positioning portion is located either distally or proximally to the catheter's elongated aperture, so that the abrasive segment of the drive shaft does not protrude laterally out of the elongated aperture.

37. The atherectomy device of claim 32 wherein the positioning wire includes alignment means for rotationally aligning the positioning wire's curved positioning portion with the catheter's elongated aperture.

38. The atherectomy device of claim 37 wherein the alignment means comprises a key and keyway, one of which is associated with the positioning wire and the other of which is associated with the catheter, thereby rotationally aligning the positioning wire with the catheter.

39. The atherectomy device of claim 38 wherein the key is carried by a slider secured to the distal portion of the positioning wire, and the keyway is formed in a wall of the catheter.

40. The atherectomy device of claim 39 wherein the slider is generally cylindrical in shape.

41. The atherectomy device of claim 32 further comprising a slider secured to the distal portion of the positioning wire.

42. The atherectomy device of claim 41 wherein the slider is generally cylindrical in shape.

43. The atherectomy device of claim 32 wherein the distal section of the catheter includes blocking means for stopping distal advancement of the distal portion of the positioning wire so that when the intermediate portion of the positioning wire and the abrasive segment of the drive shaft are both aligned with the aperture in the wall of the catheter, then further advancement of the proximal portion of the positioning wire will cause further lateral deflection of the intermediate portion of the positioning wire, thereby urging the abrasive segment of the drive shaft further laterally out through the catheter aperture to engage tissue to be removed from a bodily passageway or cavity.

44. The atherectomy device of claim 43 wherein the intermediate portion of the positioning wire has greater flexibility than the proximal portion of the positioning wire.

45. The atherectomy device of claim 44 wherein the intermediate portion of the positioning wire is of a diameter that is less than the diameter of the proximal portion of the positioning wire.

46. The atherectomy device of claim 43 wherein the blocking means comprises a plug in the catheter's drive shaft lumen located distally of the elongated aperture.

47. The atherectomy device of claim 43 further comprising a slider secured to the distal portion of the positioning wire, the slider being engagable against the plug in the catheter's drive shaft lumen to prevent distal movement of the slider past the plug.

48. The atherectomy device of claim 47 wherein the slider is generally cylindrical in shape.

49. The atherectomy device of claim 47 wherein the slider includes a key, and the catheter has a complementary keyway for rotationally aligning the intermediate curved positioning portion of the positioning wire with the elongated aperture of the catheter.

50. The atherectomy device of claim 43 wherein the blocking means comprises a complementary peg and longitudinal slot, one of which is associated with the catheter and the other of which is associated with the positioning wire, the longitudinal slot having a distal end so that engagement of the peg with the end of the slot stops distal advancement of the distal portion of the positioning wire.

51. The atherectomy device of claim 50 wherein the longitudinal slot is formed in the catheter wall, and the peg extends radially outwardly from a slider which is secured to the positioning wire and is slidably disposed within the catheter's drive shaft lumen.

52. The atherectomy device of claim 51 wherein the slider is generally cylindrical in shape.

53. The atherectomy device of claim 32 further comprising a generally cylindrical slider secured to the distal portion of the positioning wire, a peg extending generally radially outwardly from the slider into a complementary longitudinal slot formed in the catheter wall, the peg and slot functioning as a key and keyway for rotationally aligning the intermediate curved positioning portion of the positioning wire with the elongated aperture of the catheter, the slot having a distal end against which the peg may abut, the peg and complementary longitudinal slot being positioned relative to one another so that when the intermediate portion of the positioning wire and the abrasive segment of the drive shaft are both aligned with the aperture in the wall of the catheter, the peg will abut the distal end of the longitudinal slot and further advancement of the proximal portion of the positioning wire will then cause further lateral deflection of the intermediate portion of the positioning wire, thereby urging the abrasive segment of the drive shaft further laterally out through the catheter aperture to engage tissue to be removed from a bodily passageway or cavity.

54. The atherectomy device of claim 53 wherein the distal end portion of the drive shaft is provided with a sleeve which is engagable with a shoulder formed in the distal section of the catheter lumen to stop proximal movement of the distal end of the drive shaft beyond the shoulder when the positioning wire is being withdrawn proximally with respect to the catheter.

55. The atherectomy device of claim 54 wherein the shoulder is formed in the distal section of the catheter by making a distal part of such distal section of the catheter with an inner diameter which is larger than the inner diameter of the remaining part of the distal section of the catheter.

56. The atherectomy device of claim 32 wherein the distal end portion of the drive shaft is provided with a sleeve which is engagable with a shoulder formed in the distal section of the catheter lumen to stop proximal movement of the distal end of the drive shaft beyond the shoulder when the positioning wire is being withdrawn proximally with respect to the catheter.

57. The atherectomy device of claim 56 wherein the shoulder is formed in the distal section of the catheter by making a distal part of such distal section of the catheter with an inner diameter which is larger than the inner diameter of the remaining part of the distal section of the catheter.

58. The atherectomy device of claim 32 wherein the distal section of the catheter includes means for securing the distal portion of the positioning wire with respect to the catheter in a position such that the curved positioning portion of the positioning wire is aligned with the aperture in the catheter wall, so that when the proximal portion of the positioning wire is advanced, then the curved positioning portion of the positioning wire becomes further deflected laterally, thereby also urging the abrasive segment of the drive shaft further laterally and out through the catheter aperture to engage tissue to be removed from a bodily passageway or cavity.

59. The atherectomy device of claim 58 wherein the lateral deflection of the curve of the predetermined curved positioning portion of the positioning wire is small enough that the abrasive segment of the drive shaft normally does not protrude out of the catheter's elongated aperture until the proximal portion of the positioning wire is advanced to cause further lateral deflection of the curved positioning portion of the positioning wire.

60. The atherectomy device of claim 58 wherein the means for securing the distal portion of the positioning wire with respect to the catheter comprises a plug in the catheter's drive shaft lumen located distally of the elongated aperture.

61. The atherectomy device of claim 58 wherein the intermediate portion of the positioning wire has greater flexibility than the proximal portion of the positioning wire.

62. The atherectomy device of claim 58 wherein the intermediate portion of the positioning wire is of a diameter that is less than the diameter of the proximal portion of the positioning wire.

63. An atherectomy device for removing tissue from a bodily passageway or cavity, comprising:

a rotational atherectomy apparatus having a flexible, elongated drive shaft with a proximal segment, an intermediate segment, and a distal segment, a portion of the intermediate segment being coated with an abrasive material to define an abrasive segment of the drive shaft, the drive shaft further including a central lumen for receipt of a positioning wire therein, around which the drive shaft may be rotated;

a positioning wire having proximal, intermediate and distal portions, the proximal portion being generally straight, the intermediate portion having a predetermined curved positioning portion such that when the abrasive segment of the drive shaft is located along the curved positioning portion, such curved portion urges the abrasive segment laterally; and a catheter having walls defining a pair of lumens, one being sized to receive a guide wire therein, and the other being sized to receive the drive shaft therein, the catheter having proximal, intermediate and distal sections, the intermediate section having an elongated aperture in the wall defining the drive shaft lumen, the aperture having a width permitting the abrasive segment of the drive shaft to extend therethrough, the distal section including blocking means for stopping distal advancement of the distal portion of the positioning wire so that when the abrasive segment of the drive shaft and the intermediate portion of the positioning wire are both aligned with the aperture in the wall of the catheter, then further advancement of the proximal portion of the positioning wire will cause further lateral deflection of the intermediate portion of the positioning wire, thereby urging the abrasive segment of the drive shaft further laterally and out through the catheter aperture to engage tissue to be removed from a bodily passageway or cavity.

64. The atherectomy device of claim 63 wherein the blocking means comprises a plug in the catheter's drive shaft lumen located distally of the elongated aperture.

65. The atherectomy device of claim 64 wherein the positioning wire includes a generally cylindrically shaped slider secured to the distal portion, the slider being engagable against the catheter plug to prevent distal movement of the cylindrical slider past the plug.

66. The atherectomy device of claim 63 wherein the blocking means comprises a complementary peg and longitudinal slot, one of which is associated with the catheter and the other of which is associated with the positioning wire, the longitudinal slot having a distal end so that engagement of the peg with the end of the slot stops distal advancement of the distal portion of the positioning wire.

67. The atherectomy device of claim 66 wherein the longitudinal slot is formed in the catheter wall, and the peg extends radially outwardly from a generally cylindrical slider secured to the positioning wire and being slidably disposed within the catheter's drive shaft lumen.

68. The atherectomy device of claim 63 wherein the intermediate portion of the positioning wire has greater flexibility than the proximal portion of the positioning wire.

69. The atherectomy device of claim 68 wherein the intermediate portion of the positioning wire is of a diameter that is less than the diameter of the proximal and distal portions of the positioning wire.

70. An atherectomy device for removing tissue from a bodily passageway or cavity, comprising:

a rotational atherectomy apparatus having a flexible, elongated drive shaft with a proximal segment, an intermediate segment, and a distal segment, a portion of the intermediate segment being coated with an abrasive material to define an abrasive segment of the drive shaft, the drive shaft further including a central lumen for receipt of a guide wire therein, around which the drive shaft may be rotated;

a guide wire having proximal, intermediate and distal portions, the proximal portion being generally straight;

a catheter having walls defining a lumen sized to receive the drive shaft therein, the catheter having proximal, intermediate and distal sections, the intermediate section having an elongated aperture in the wall, the aperture having a width permitting the abrasive segment of the drive shaft to extend therethrough, the distal section including blocking means for stopping distal advancement of the distal portion of the guide wire so that when the abrasive segment of the drive shaft and the intermediate portion of the guide wire are both aligned with the aperture in the wall of the catheter, then further advancement of the proximal portion of the guide wire will cause lateral deflection of the intermediate portion of the guide wire, thereby urging the abrasive segment of the drive shaft laterally out through the catheter aperture to engage tissue to be removed from a bodily passageway or cavity.

71. An atherectomy device for removing tissue from a bodily passageway or cavity, comprising:

a rotational atherectomy apparatus having a flexible, elongated drive shaft with a proximal segment, an intermediate segment, and a distal segment, a portion of the intermediate segment being coated with an abrasive material to define an abrasive segment of the drive shaft, the drive shaft further including a central lumen for receipt of a positioning wire therein, around which the drive shaft may be rotated;

a positioning wire having proximal, intermediate and distal portions, the proximal portion being generally straight, the intermediate portion having a predetermined curved positioning portion such that when the abrasive segment of the drive shaft is located along the curved positioning portion, such curved portion urges the abrasive segment laterally; and a catheter having walls defining a pair of lumens, one being a guide wire lumen sized to receive a guide wire therein, and the other being a drive shaft lumen sized to receive the drive shaft therein, the catheter having proximal, intermediate and distal sections, the intermediate section having an elongated aperture in the wall defining the drive shaft lumen, the aperture having a width permitting the abrasive segment of the drive shaft to extend therethrough;

the distal section of the catheter including means for securing the distal portion of the positioning wire with respect to the catheter in a position such that the curved positioning portion of the positioning wire is aligned with the aperture in the catheter wall, so that when the proximal portion of the positioning wire is advanced, then the curved positioning portion of the positioning wire becomes further deflected laterally, thereby also urging the abrasive segment of the drive shaft further laterally and out through the catheter aperture to engage tissue to be removed from a bodily passageway or cavity.

72. An atherectomy device for removing tissue from a bodily passageway or cavity, comprising:

a rotational atherectomy apparatus having a flexible, elongated drive shaft with a proximal segment, an intermediate segment, and a distal segment, a portion of the intermediate segment being coated with an abrasive material to define an abrasive segment of the drive shaft, the drive shaft further including a central lumen for receipt of a guide wire therein, around which the drive shaft may be rotated;

a guide wire having proximal, intermediate and distal portions, the proximal portion being generally straight, the intermediate portion having a predetermined curved positioning portion such that when the abrasive segment of the drive shaft is located along the curved positioning portion, such curved portion urges the abrasive segment laterally; and a catheter having side walls defining an outer surface and a drive shaft lumen sized to receive the drive shaft therein, the catheter having proximal, intermediate and distal sections, the intermediate section having an elongated aperture in the side wall, the aperture having a width permitting the abrasive segment of the drive shaft to extend therethrough so that when the abrasive segment of the drive shaft and the curved positioning portion of the guide wire are both aligned with the aperture in the side wall of the catheter, such curved positioning portion urges the abrasive segment laterally out through the catheter aperture to engage tissue to be removed from a bodily passageway or cavity;

the intermediate section of the catheter including ultrasound transducers for imaging tissue surrounding the intermediate section of the catheter.

73. The atherectomy device of claim 72 wherein at least some of the ultrasound transducers are positioned to image radially outwardly from the catheter's outer surface.

74. The atherectomy device of claim 72 wherein at least some of the ultrasound transducers are positioned to image from the surface of the catheter drive shaft lumen and through the catheter aperture.

75. An atherectomy device for removing tissue from a bodily passageway or cavity, comprising:

a rotational atherectomy apparatus having a flexible, elongated drive shaft with a proximal segment, an intermediate segment, and a distal segment, a portion of the intermediate segment being coated with an abrasive material to define an abrasive segment of the drive shaft, the drive shaft further including a central lumen for receipt of a positioning wire therein, around which the drive shaft may be rotated;

a positioning wire having proximal, intermediate and distal portions, the proximal portion being generally straight, the intermediate portion having a predetermined curved positioning portion such that when the abrasive segment of the drive shaft is located along the curved positioning portion, such curved portion urges the abrasive segment laterally; and a catheter having walls defining an outer surface and a pair of lumens, one being a guide wire lumen sized to receive a guide wire therein, and the other being a drive shaft lumen sized to receive the drive shaft therein, the catheter having proximal, intermediate and distal sections, the intermediate section having an elongated aperture in the wall defining the drive shaft lumen, the aperture having a width permitting the abrasive segment of the drive shaft to extend therethrough so that when the abrasive segment of the drive shaft and the curved positioning portion of the positioning wire are both aligned with the aperture in the wall of the catheter, such curved positioning portion urges the abrasive segment laterally out through the catheter aperture to engage tissue to be removed from a bodily passageway or cavity;

the intermediate section of the catheter including ultrasound transducers for imaging tissue surrounding the intermediate section of the catheter.

76. The atherectomy device of claim 75 wherein at least some of the ultrasound transducers are positioned to image radially outwardly from the catheter's outer surface.

77. The atherectomy device of claim 75 wherein at least some of the ultrasound transducers are positioned to image from the surface of the catheter drive shaft lumen and through the catheter aperture.

* * * * *